US008691533B2

(12) United States Patent
Notka et al.

(10) Patent No.: US 8,691,533 B2
(45) Date of Patent: Apr. 8, 2014

(54) INDUCIBLE GENE EXPRESSION

(75) Inventors: Frank Notka, Regensburg (DE); Ralf Wagner, Regensburg (DE); Diana Hammer, Regensburg (DE)

(73) Assignee: GeneArt AG, Regensburg (DE)

( * ) Notice: Subject to any disclaimer, the term of this patent is extended or adjusted under 35 U.S.C. 154(b) by 1856 days.

(21) Appl. No.: 11/658,206

(22) PCT Filed: Aug. 3, 2005

(86) PCT No.: PCT/EP2005/008427

§ 371 (c)(1),
(2), (4) Date: Jan. 23, 2007

(87) PCT Pub. No.: WO2006/013103

PCT Pub. Date: Feb. 9, 2006

(65) Prior Publication Data

US 2011/0033429 A1 Feb. 10, 2011

(30) Foreign Application Priority Data

Aug. 3, 2004 (DE) ........................ 10 2004 037 611

(51) Int. Cl.

*C12N 5/10* (2006.01)
*C12N 7/01* (2006.01)
*C12N 15/00* (2006.01)
*C12N 15/33* (2006.01)
*A61K 48/00* (2006.01)

(52) U.S. Cl.

USPC .................... 435/69.7; 435/235.1; 435/320.1; 435/325; 514/44; 536/23.4

(58) Field of Classification Search

USPC ............ 435/69.7, 235.1, 320.1, 325; 514/44; 536/23.4

See application file for complete search history.

(56) References Cited

FOREIGN PATENT DOCUMENTS

| | | | | |
|---|---|---|---|---|
| EP | 1 156 112 A1 * | 11/2001 | ............ | C12N 15/48 |
| WO | WO98/03669 | 1/1998 | | |
| WO | WO98/34640 | 8/1998 | | |
| WO | WO 00/39304 * | 7/2000 | ............ | C12N 15/49 |

OTHER PUBLICATIONS

Ding et al, Frontiers in Bioscience 7:a15-28, 2002.*

Bunnell et al., "Gene therapy for infectious diseases", *Clinical Microbiology Reviews*, vol. 11, No. 1, 1998, 42-58.

Cara et al., "Inhibition of HIV-1 Replication by Combined Expression of Gag Dominant Negative Mutant and a Human Ribonuclease in a Tightly Controlled HIV-1 Inducible Vector", *Gene Therapy*, vol. 5, No. 1, Jan. 1998, 65-75.

Caruso et al., "Selective killing of CD4+ cells harboring a human immunodeficiency virus-inducible suicide gene prevents viral spead in an infected cell population", *Proceedings of the National Academy of Sciences*, vol. 89, No. 1, Jan. 1, 1992, 182-186.

Chang et al., "Regulation by HIV Rev depends upon recognition of splice sites", *Cell*, vol. 59, No. 5, Dec. 1, 1989, 789-795.

Chen et al., "mRNA decay mediated by two distinct AU-rich elements from c-fos and granulocyte-macrophage colony-stimulating factor transcripts: different deadenylation kinetics and uncoupling from translation", *Molecular and Cellular Biology*, vol. 15, No. 10, Oct. 1995, 5777-5788.

Chiu et al., "Effects of gag mutations on human immunodeficiency virus type 1 particle assembly, processing, and cyclophilin A incorporation.", *Journal of Medical Virology*, vol. 68, No. 2, Oct. 2002, 156-163.

Cochrane et al., "Identification and characterization of intragenic sequences which repress human immunodeficiency virus structual gene expression", *Journal of Virology*, vol. 65, No. 10, Oct. 1991, 5305-5313.

Facke et al., "A large deletion in the matrix domain of the human immunodeficiency virus gag gene redirects virus particle assembly from the plasma membrane to the endoplasmic reticulum", *Journal of Virology*, vol. 67, No. 8, Aug. 1993, 4972-4980.

Furuta et al., "HIV-1 capsid mutants inhibit the replication of wild-type virus at both early and late infection phases", *FEBS Letters*, vol. 415, No. 2, Sep. 29, 1997, 231-234.

Gallina et al., "Influence of MA internal sequences, but not of the myristylated N-terminus sequence, on the budding site of HIV-1 Gag protein,", *Biochimica et Biophysica Res. Commun.*, vol. 204, No. 3, Nov. 15, 2004, 1031-1038.

Graf et al., "Concerted Action of Multiple Cis-Acting Sequences is Required for Rev Dependence of Late Human Immunodeficiency Virus Type 1 Gene Expression", *Journal of Virology*, vol. 74, Issue 22,, Nov. 2000, 10822-10826.

Graham et al., "Transformation of rat cells by DNA of human adenovirus", *Virology*, vol. 54, No. 2, 1973, 536-539.

Harrison et al., "Inhibition of HIV production in cells containing an integratedm HIV-regulated diphtheria toxin A chain gene", *AIDS Research and Human Retroviruses*, vol. 8, No. 1, Jan. 1992, 39-45.

Kimpton et al., "Detection of replication-competent and pseudotyped human immunodeficiency virus with a sensitive cell line on the basis of activation of an integrated beta-galactosidase gene", *Journal of Virology*, vol. 66, No. 4, Apr. 1992, 2232-2239.

Kjems et al., "The basic domain of Rev from human immunodeficiency virus type 1 specificaly blocks the entry of U4/U6. US small nuclear ribonucleoprotein in spliceosome assembly", *Journal of Virology*, vol. 67, No. 8, Aug. 1993, 4769-4776.

Kotsopoulou et al., "A Rev-Independent Human Immunodeficiency Virus Type 1 (HIV-1)-Based Vector That Exploits a Codon-Optimized HIV-1 Gag-Pol Gene", *Journal of Virology*, vol. 74, Issue 10, 2000, 4839-4852.

Laemmli et al., "Cleavage of Structural Proteins during the Assembly of the Head of Bacteriophage T4", *Nature*, vol. 227, Issue 5259,, Aug. 15, 1970, 680-685.

Liu et al., "Regulated expression of a dominant negative form of Rev improves resistance to HIV replication in T cells", *Gene Therapy*, vol. 1, No. 1, Jan. 1994, 32-37.

Lu et al., "U1 small nuclear RNA plays a direct role in the formation of a rev-regulated human immunodeficiency virus env mRNA that remains unspliced", *Proceedings of the National Academy of Sciences*, vol. 87, No. 19, Oct. 1990, 7598-7602.

(Continued)

*Primary Examiner* — Kevin Hill

(57) ABSTRACT

The invention relates to vector constructs for an HIV-specific gene therapy. The expression of transgenes is coupled with an infection of the cell with HIV while the transcription of the transgene is controlled by a transcription control region derived from HIV. In addition, the transgene is improved with regard to RNA stability and expression efficiency by modifying the nucleotide sequence.

5 Claims, 9 Drawing Sheets

(56) References Cited

OTHER PUBLICATIONS

Maldarelli et al., "Identification of postranscriptionally active inhibitory sequences in human immunodeficiency virus type 1 RNA: novel level of gene regulation", *Journal of Virology*, vol. 65, No. 11, Nov. 1991, 5732-5743.
Marcello et al., "Inducible expression of herpes simplex virus thymidine kinase form a bicistronic HIV1 vector", *Research in Virology*, vol. 149, No. 6, Nov.-Dec. 1998, 419-431.
Mauttino et al., "Gene threrapy of HIV-1 infection using lentiviral vectors expression anti-HIV-1 genes", *AIDS Patient Care STDS*, vol. 16, No. 1, Jan. 2002, 11-26.
Mikaelian et al., "Interactions of INS (CRS) elements and the splicing machinery regulate the production of Rev-responsive mRNAs", *Journal of Molecular Biology*, vol. 257, No. 2, Mar. 29, 1996, 246-264.
Miyake et al., "Selective killing of human immunodeficiency virus-infected cells by targeted gene transfer and inducible gene expression using a recombinant human immunodeficiency virus vector", *Human Gene Therapy*, vol. 12, No. 3, Feb. 2001, 227-333.
Muratori et al., "Inducible expression of deltaNGFr/F12Nef fusion protein as a new tool for anti-human immunodeficiency virus type 1 gene therapy", *Human Gene Therapy*, vol. 13, No. 14, Sep. 20, 2002, 1751-1766.
Nasioulas et al., "Elements distinct from human immunodeficiency virus type 1 splice sites are responsible for the Rev dependence of any mRNA", *Journal of Virology*, vol. 68, No. 5, May 1994, 2988-2993.
Olsen et al., "Interaction of cellular factors with intragenic cis-acting repressive sequences within the HIV genome", *Virology*, vol. 191, 1992, 709-715.
Ono et al., "Cell-type-dependent targeting of human immunodeficiency virus type 1 assembly to the plasma membrane and the multivesicular body", *Journal of Virology*, vol. 78, No. 3, Feb. 2004, 1552-1563.
O'Reilly et al., "Two strong 5' splice sites and competing, suoptimal 3' splice sites involved in alternative splicing of human immunodeficiency virus type 1 RNA", *Virology*, vol. 213, 1995, 373-385.
Pollard et al., "The HIV-1 Rev protein", *Annual Reviews in Microbiology*, vol. 52, Oct. 1998, 491-532.
Powell et al., "HIV Rev-dependent binding of SF2/ASF to the Rev response element: possible role in Rev-mediated inhibition of HIV RNA splicing", *Proceedings of the National Academy of Sciences*, vol. 84, No. 3, Feb. 4, 1997, 973-978.
Ragheb et al., "Inhibition of human immunodeficiency virus type 1 by Tat/Rev-regulated expression of cytosine deaminase, interferon alpha2, or diphtheria toxin compared with inhibition by transdominant Rev.", *Human Gene Therapy*, vol. 10, No. 1, Jan. 1, 1999, 103-112.
Ratner et al., "Complete nucleotide sequences of functional clones of the AIDS virus.", *AIDS Research and Human Retroviruses*, vol. 3, No. 1, Spring 1987, 57-69.
Rosen et al., "Intragenic cis-acting art gene-responsive sequences of the human immunodeficiency virus", *Proceedings of the National Academy of Sciences*, vol. 85, No. 7, Apr. 1, 1988, 2071-2075.
Schneider et al., "Inactivation of the human immunodeficiency virus type 1 inhibitory elements allows Rev-independent expression of Gag and Gag/protease and particle formation", *Journal of Virology*, vol. 71, No. 7, Jul. 1997, 4892-4903.
Schwartz et al., "Distinct RNA sequences in the gag region of human immunodeficiency virus type 1 decreases RNA stability and inhibit expression in the absence of Rev protein", *Journal of Virology*, vol. 66, No. 1, Jan. 1992, 150-159.
Schwartz et al., "Mutational inactivation of an inhibitory sequence in human immunodeficiency virus type 1 results in Rev-independent gag expression", *Journal of Virology*, vol. 66, No. 12, Dec. 1992, 7176-7182.
Smythe et al., "A Rev-inducible mutant gag gene stably transferred into T lymphocytes: an approach to gene therapy against human immunodeficiency virus type 1 infection", *Proceedings of the National Academy of Sciences*, vol. 91, No. 9,, Apr. 1994, 3657-3661.
Trono et al., "HIV-1 Gag mutants can dominantly interfere with the replication of the wild-type virus", *Cell*, vol. 59, No. 1, Oct. 6, 1989, 113-120.
Von Poblotzki et al., "Identification of a region in the Pr55gag-polyprotein essential for HIV-1 particle formation", *Virology*, vol. 193, No. 2, Apr. 1993, 981-985.
Wagner et al., "Rev-independent expression of synthetic gag-pol genes of human immunodeficiency virus type 1 and simian immunodeficiency virus: implications for the safety of lentiviral vectors.", *Human Gene Therapy*, vol. 11, No. 17, Nov. 20, 2000, 2403-2413.
Wilk et al., "Organization of immature human immunodeficiency virus type 1", *Journal of Virology*, vol. 75, No. 2, 2001, 759-771.
Wolf et al., "Production, Mapping, and Biological Characterisation of Monoclonal Antibodies to the Core Protein (p24) of the Human Immunodeficiency Virus Type 1", *AIFO 1*, AIDS-Forsch, vol. 1,, 1990, 24-29.
Zolotukhin et al., "A "humanized" Green Fluorescent Protein cDNA Adapted for High-Level Expression in Mammalian Cells.", *Journal of Virology*, vol. 70, 1996, 4646-4654.

* cited by examiner

A

B

A

B

SEQ Ids and alignments of the employed DNA sequences

SEQ-ID of the specified constructs:

SEQ-ID1: TDsyngag:

```
1      GAATTCGCCG CCAGCATGGG CGCCAGGGCC AGCGTGCTGA GCGGCGGCGA GCTGGACAGG
61     TGGGAGAAGA TCAGGCTGAG GCCCGGCGGC AAGAAGAAGT ATAAGCTGAA GCACATCGTG
121    TGGGCCAGCA GGGAGCTGGA GAGGTTCGCC GTGAACCCCG GCCTGCTGGA GACCAGCGAG
181    GGCTGCAGGC AGATCCTGGG CCAGCTGCAG CCCAGCCTGC AGACCGGCAG CGAGGAGCTG
241    AGGAGCCTGT ACAACACCGT GGCCACCCTG TACTGCGTGC ACCAGAGGAT CGAGATCAAG
301    GACACCAAGG AGGCCCTGTT CAGCCCCGAG GTGATCCCCA TGTTCAGCGC CCTGAGCGAG
361    GGAGCCACCC CCCAGGACCT GAACACCATG CTGAACACCG TGGGCGGCCA CCAGGCCGCC
421    ATGCAGATGC TGAAGGAGAC CATCAACGAG GAGGCCGCCG AGTGGGACAG GGTGCACCCC
481    GTGCACGCCG GCCCCATCGC CCCCGGCCAG ATGAGGGAGC CCCGCGGCAG CGACATCGCC
541    GGCACCACCA GCACCCTGCA GGAGCAGATC GGCTGGATGA CCAACAACCC CCCCATCCCC
601    GTGGGCGAAA TCTACAAGAG GTGGATCATC CTGGGCCTGA ACAAGATCGT GAGGATGTAC
661    AGCCCCACCA GCATCCTGGA TATCAGGCAG GGCCCCAAAG AGCCCTTCAG GGACTACGTG
721    GACAGGTTCT ACAAGACCCT GCGCGCCGAG CAGGCCAGCC AGGAGGTGAA GAACTGGATG
781    ACCGAGACCC TGCTGGTGCA GAACGCCAAC CCCGACTGCA AGACCATCCT GAAGGCCCTG
841    GGACCCGCCG CCACCCTGGA GGAGATGATG ACCGCCTGCC AGGGCGTGGG CGGCCCCGGC
901    CACAAGGCCA GGGTGCTGGC CGAGGCCATG AGCCAGGTGA CCAACACCGC CACCATCATG
961    ATGCAGAGGG GCAACTTCAG GAACCAGAGG AAGATGGTGA AGTGCTTCAA CTGCGGCAAG
1021   GAGGGCCACA CCGCCAGGAA CTGCCGCGCC CCCAGGAAGA AGGGCTGCTG GAAGTGCGGC
1081   AAGGAGGGCC ACCAGATGAA GGACTGCACC GAGAGGCAGG CCAACTAATA GTCCGGACTC
1141   GAG
```

SEQ ID3: TDwtgag (coding region):

```
1      ATGGGTGCGA GAGCGTCAGT ATTAAGCGGG GGAGAATTAG ATCGATGGGA AAAAATTCGG
61     TTAAGGCCAG GGGGAAAGAA AAAATATAAA TTAAAACATA TAGTATGGGC AAGCAGGGAG
121    CTAGAACGAT TCGCAGTTAA TCCTGGCCTG TTAGAAACAT CAGAAGGCTG TAGACAAATA
181    CTGGGACAGC TACAACCATC CCTTCAGACA GGATCAGAAG AACTTAGATC ATTATATAAT
241    ACAGTAGCAA CCCTCTATTG TGTGCATCAA AGGATAGAGA TAAAAGACAC CAAGGAAGCT
301    TTATTCAGCC CAGAAGTAAT ACCCATGTTT TCAGCATTAT CAGAAGGAGC CACCCCACAA
361    GATTTAAACA CCATGCTAAA CACAGTGGGG GGACATCAAG CAGCCATGCA AATGTTAAAA
421    GAGACCATCA ATGAGGAAGC TGCAGAATGG GATAGAGTAC ATCCAGTGCA TGCAGGGCCT
481    ATTGCACCAG GCCAGATGAG AGAACCAAGG GGAAGTGACA TAGCAGGAAC TACTAGTACC
541    CTTCAGGAAC AAATAGGATG GATGACAAAT AATCCACCTA TCCCAGTAGG AGAAATTTAT
601    AAAAGATGGA TAATCCTGGG ATTAAATAAA ATAGTAAGAA TGTATAGCCC TAGCAGCATT
661    CTGGACATAA GACAAGGACC AAAAGAACCT TTTAGAGACT ATGTAGACCG GTTCTATAAA
721    ACTCTAAGAG CCGAGCAAGC TTCACAGGAG GTAAAAAATT GGATGACAGA AACCTTGTTG
781    GTCCAAAATG CGAACCCAGA TTGTAAGACT ATTTTAAAAG CATTGGGACC AGCGGCTACA
841    CTAGAAGAAA TGATGACAGC ATGTCAGGGA GTAGGAGGAC CCGGCCATAA GGCAAGAGTT
901    TTGGCTGAAG CAATGAGCCA AGTAACAAAT ACAGCTACCA TAATGATGCA GAGAGGCAAT
961    TTTAGGAACC AAAGAAAGAT GGTTAAGTGT TTCAATTGTG GCAAAGAAGG GCACACAGCC
1021   AGAAATTGCA GGGCCCCTAG GAAAAAGGGC TGTTGGAAAT GTGGAAAGGA AGGACACCAA
1081   ATGAAAGATT GTACTGAGAG ACAGGCTAAT TAA
```

Alignment TDwtgag:TDsyngag (coding region)

TDwtgag:TDsyngag identity= 72.78%(821/1128) gap=0.00%(0/1128)

```
1    ATGGGTGCGAGAGCGTCAGTATTAAGCGGGGGAGAATTAGATCGATGGGAAAAAATTCGG
     ||||| || || ||     ||  | ||||| || ||   | ||   | ||||| || ||  ||
1    ATGGGCGCCAGGGCCAGCGTGCTGAGCGGCGGCGAGCTGGACAGGTGGGAGAAGATCAGG

61   TTAAGGCCAGGGGGAAAGAAAAAATATAAATTAAAACATATAGTATGGGCAAGCAGGGAG
      | ||||| || || ||||| || |||||  | || || || || ||||| |||||||||
```

FIG. 6

```
61   CTGAGGCCCGGCGGCAAGAAGAAGTATAAGCTGAAGCACATCGTGTGGCCAGCAGGGAG

121  CTAGAACGATTCGCAGTTAATCCTGGCCTGTTAGAAACATCAGAAGGCTGTAGACAAATA
121  CTGGAGAGGTTCGCCGTGAACCCCGGCCTGCTGGAGACCAGCGAGGGCTGCAGGCAGATC

181  CTGGGACAGCTACAACCATCCCTTCAGACAGGATCAGAAGAACTTAGATCATTATATAAT
181  CTGGGCCAGCTGCAGCCCAGCCTGCAGACCGGCAGCGAGGAGCTGAGGAGCCTGTACAAC

241  ACAGTAGCAACCCTCTATTGTGTGCATCAAAGGATAGAGATAAAAGACACCAAGGAAGCT
241  ACCGTGGCCACCCTGTACTGCGTGCACCAGAGGATCGAGATCAAGGACACCAAGGAGGCC

301  TTATTCAGCCCAGAAGTAATACCCATGTTTTCAGCATTATCAGAAGGAGCCACCCCACAA
301  CTGTTCAGCCCCGAGGTGATCCCCATGTTCAGCGCCCTGAGCGAGGGAGCCACCCCCCAG

361  GATTTAAACACCATGCTAAACACAGTGGGGGACATCAAGCAGCCATGCAAATGTTAAAA
361  GACCTGAACACCATGCTGAACACCGTGGGCGGCCACCAGGCCGCCATGCAGATGCTGAAG

421  GAGACCATCAATGAGGAAGCTGCAGAATGGGATAGAGTACATCCAGTGCATGCAGGGCCT
421  GAGACCATCAACGAGGAGGCCGCCGAGTGGGACAGGGTGCACCCCGTGCACGCCGGCCCC

481  ATTGCACCAGGCCAGATGAGAGAACCAAGGGGAAGTGACATAGCAGGAACTACTAGTACC
481  ATCGCCCCCGGCCAGATGAGGGAGCCCCGCGGCAGCGACATCGCCGGCACCACCAGCACC

541  CTTCAGGAACAAATAGGATGGATGACAAATAATCCACCTATCCCAGTAGGAGAAATTTAT
541  CTGCAGGAGCAGATCGGCTGGATGACCAACAACCCCCCCATCCCCGTGGGCGAAATCTAC

601  AAAAGATGGATAATCCTGGGATTAAATAAAATAGTAAGAATGTATAGCCCTACCAGCATT
601  AAGAGGTGGATCATCCTGGGCCTGAACAAGATCGTGAGGATGTACAGCCCCACCAGCATC

661  CTGGACATAAGACAAGGACCAAAAGAACCTTTTAGAGACTATGTAGACCGGTTCTATAAA
661  CTGGATATCAGGCAGGGCCCCAAAGAGCCCTTCAGGGACTACGTGGACAGGTTCTACAAG

721  ACTCTAAGAGCCGAGCAAGCTTCACAGGAGGTAAAAAATTGGATGACAGAAACCTTGTTG
721  ACCCTGCGCGCCGAGCAGGCCAGCCAGGAGGTGAAGAACTGGATGACCGAGACCCTGCTG

781  GTCCAAAATGCGAACCCAGATTGTAAGACTATTTTAAAAGCATTGGGACCAGCGGCTACA
781  GTGCAGAACGCCAACCCCGACTGCAAGACCATCCTGAAGGCCCTGGGACCCGCCGCCACC

841  CTAGAAGAAATGATGACAGCATGTCAGGGAGTAGGAGGACCCGGCCATAAGGCAAGAGTT
841  CTGGAGGAGATGATGACCGCCTGCCAGGGCGTGGGCGGCCCCGGCCACAAGGCCAGGGTG

901  TTGGCTGAAGCAATGAGCCAAGTAACAAATACAGCTACCATAATGATGCAGAGAGGCAAT
901  CTGGCCGAGGCCATGAGCCAGGTGACCAACACCGCCACCATCATGATGCAGAGGGGCAAC

961  TTTAGGAACCAAAGAAAGATGGTTAAGTGTTTCAATTGTGGCAAAGAAGGGCACACAGCC
961  TTCAGGAACCAGAGGAAGATGGTGAAGTGCTTCAACTGCGGCAAGGAGGGCCACACCGCC
```

FIG. 6 CONT.

```
1021  AGAAATTGCAGGGCCCCTAGGAAAAAGGGCTGTTGGAAATGTGGAAAGGAAGGACACCAA
      || || ||| | ||||| ||||| |||||||| ||||| || || ||||| || ||||| 
1021  AGGAACTGCCGCGCCCCCAGGAAGAAGGGCTGCTGGAAGTGCGGCAAGGAGGGCCACCAG

1081  ATGAAAGATTGTACTGAGAGACAGGCTAATTAA
      ||||| || || || ||||| ||||| || |||
1081  ATGAAGGACTGCACCGAGAGGCAGGCCAACTAA
```

SEQ-ID 16: TDsyngag delta 2:

```
1    ATGGGCGCCA GGGCCAGCGT GCTGAGCGGC GGCGAGCTGG ACAGGTGGGA GAAGATCAGG
61   CTGAGGCCCG GCGGCAAGAA GAAGTATAAG CTGAAGCACA TCGTGTGGGC CAGCAGGGAG
121  CTGGAGAGGT TCGCCGTGAA CCCCGGCCTG CTGGAGACCA GCGAGGGCTG CAGGCAGATC
181  CTGGGCCAGC TGCAGCCCAG CCTGCAGACC GGCAGCGAGG AGCTGAGGAG CCTGTACAAC
241  ACCGTGGCCA CCCTGTACTG CGTGCACCAG AGGATCGAGA TCAAGGACAC CAAGGAGGCC
301  CTGTTCAGCC CCGAGGTGAT CCCCATGTTC AGCGCCCTGA GCGAGGGAGC CACCCCCCAG
361  GACCTGAACA CCATGCTGAA CACCGTGGGC GGCCACCAGG CCGCCATGCA GATGCTGAAG
421  GAGACCATCA ACGAGGAGGC CGCCGAGTGG GACAGGGTGC ACCCCGTGCA CGCCGGCCCC
481  ATCGCCCCCG GCCAGATGAG GGAGTACAAG ACCCTGCGCG CCGAGCAGGC CAGCCAGGAG
541  GTGAAGAACT GGATGACCGA GACCCTGCTG GTGCAGAACG CCAACCCCGA CTGCAAGACC
601  ATCCTGAAGG CCCTGGGACC CGCCGCCACC CTGGAGGAGA TGATGACCGC CTGCCAGGGC
661  GTGGGCGGCC CCGGCCACAA GGCCAGGGTG CTGGCCGAGG CCATGAGCCA GGTGACCAAC
721  ACCGCCACCA TCATGATGCA GAGGGGCAAC TTCAGGAACC AGAGGAAGAT GGTGAAGTGC
781  TTCAACTGCG GCAAGGAGGG CCACACCGCC AGGAACTGCC GCGCCCCCAG GAAGAAGGGC
841  TGCTGGAAGT GCGGCAAGGA GGGCCACCAG ATGAAGGACT GCACCGAGAG GCAGGCCAAC
```

SEQ-ID 18: TDsyngag delta 2 delta p7:

```
1    ATGGGCGCCA GGGCCAGCGT GCTGAGCGGC GGCGAGCTGG ACAGGTGGGA GAAGATCAGG
61   CTGAGGCCCG GCGGCAAGAA GAAGTATAAG CTGAAGCACA TCGTGTGGGC CAGCAGGGAG
121  CTGGAGAGGT TCGCCGTGAA CCCCGGCCTG CTGGAGACCA GCGAGGGCTG CAGGCAGATC
181  CTGGGCCAGC TGCAGCCCAG CCTGCAGACC GGCAGCGAGG AGCTGAGGAG CCTGTACAAC
241  ACCGTGGCCA CCCTGTACTG CGTGCACCAG AGGATCGAGA TCAAGGACAC CAAGGAGGCC
301  CTGTTCAGCC CCGAGGTGAT CCCCATGTTC AGCGCCCTGA GCGAGGGAGC CACCCCCCAG
361  GACCTGAACA CCATGCTGAA CACCGTGGGC GGCCACCAGG CCGCCATGCA GATGCTGAAG
421  GAGACCATCA ACGAGGAGGC CGCCGAGTGG GACAGGGTGC ACCCCGTGCA CGCCGGCCCC
481  ATCGCCCCCG GCCAGATGAG GGAGTACAAG ACCCTGCGCG CCGAGCAGGC CAGCCAGGAG
541  GTGAAGAACT GGATGACCGA GACCCTGCTG GTGCAGAACG CCAACCCCGA CTGCAAGACC
601  ATCCTGAAGG CCCTGGGACC CGCCGCCACC CTGGAGGAGA TGATGACCGC CTGCCAGGGC
661  GTGGGCGGCC CCGGCCACAA GGCCAGGGTG CTGGCCGAGG CCATGAGCCA GGTGACCAAC
721  ACCGCCACCA TCATGATGCA GAGGGGCAAC TTCAGGAACC AGAGGAAGAT GGTGAAGTGC
781  TTCAACTGCG GCAAGGAGGG CCACACCGCC AGGAACTGCC GCGCCCCCAG GAAGAAGGGC
841  TGCTGGAAGT GCGGCAAGGA GGGCCACCAG ATGAAGGACT GCACCGAGAG GCAGGCCAAC
```

INDUCIBLE GENE EXPRESSION

This is a §371 of PCT/EP2005/008427 filed Aug. 3, 2005, which claims priority from German Patent Application No. 10 2004 037 611.5 filed Aug. 3, 2004.

The present invention relates to a method for inducible gene expression, in which a target nucleic acid sequence to be expressed is modified at the nucleic acid level so that an increase in the expression is achieved, and the nucleic acid sequence modified in this way is expressed under the control of an inducible transcription control sequence.

Many types of viruses are involved in an active export of their incompletely spliced transcripts from the cell nucleus of the infected host cell. This can take place either via the use of a cis-position RNA signal within the viral transcripts (constitutive transport elements) or occurs with the help of viral proteins.

Cis-active transport elements are used for example from MPMV-CTE (Mason-Pfizer Monkey Virus constitutive transport element), SRV-CTE (Simian Retrovirus constitutive transport element), Hepatitis B-Virus PRE (posttranscriptional regulatory element) and HSV (Herpes Simplex Virus) (within the TK (thymidine kinase) gene). These RNA elements recruit cellular factors and export pathways in order to allow the nuclear export of the viral transcripts.

As an alternative, the nuclear export can also be mediated via an export factor that binds specifically to a target sequence within the viral transcripts and transports these in co-operation with cellular factors into the cytoplasm. Thus, for example, Ad-5 (Adenovirus 5) transcripts are exported with the aid of the 34K and E4orf6 proteins, EBV (Epstein-Barr Virus) transcripts with the aid of the EB2 protein, Herpes virus Saimiri transcripts with the aid of the ORF 57 gene product, HSV transcripts with the aid of the ICP 27 protein, HTLV-I and II (human T-cell Leukemia Virus I and II) transcripts with the aid of the Rex proteins, EIAV (Equine Infectious Anaemia Virus), SIV (Simian Immunodeficiency Virus) and HIV-1 and HIV-2 (Human Immunodeficiency Virus 1 and 2) transcripts with the aid of the Rev proteins.

The HIV-1 Rev-mediated nuclear export of subsequent HIV-1 transcripts has been investigated best. Like all Lentiviruses, HIV-1 is involved in activating several genes from only one proviral matrix and expressing them in a time-specified sequence. By alternative splicing events as well as further regulation mechanisms occurring at the RNA level, different genes are generated from only one ~9 kb long primary transcript. These viral transcripts may be subdivided into three classes according to their size, namely ~9 kb unspliced (gag, pol), ~4 kb singly spliced (env, vif, vpr, vpu) and ~2 kb multiply spliced (rev, tat, nef) RNAs.

Apart from the occurrence of incompletely to multiply spliced transcripts, a time sequence in the expression of these different RNA species may also be observed. Thus, in the early phase of the replication in the cytoplasm of the infected cells, only the multiply spliced ~2 kb RNAs and their gene products Rev, Tat and Nef can be detected. Only after a time delay are the unspliced (~9 kb) and singly spliced (~4 kb) transcripts and their gene products Gag, Pol and Env then also observed.

In cells that have been infected with virus mutants lacking an active Rev protein, the singly spliced and unspliced transcripts can be detected, but never in the cytoplasm. The unpsliced and singly spliced transcripts then accumulate in the nucleus and the subsequent structure proteins (Gag, Env) and enzymes (Pol) translated from them cannot be formed. The viral Rev protein is thus involved in an essential way in the time-regulated expression of the viral genes.

HIV-1 Rev, like the RNA transport molecules listed above, are shuttle proteins which transport viral RNAs from the nucleus to the cytoplasm via the interaction with an RNA target sequence located within viral transcripts. Thus, HIV-1 Rev binds in the nucleus specifically to its RNA target structure RRE, the "Rev-responsive-element". This 351nucleotide (nt) long region is localised within the Env reading frame and is thus a constituent of all unspliced and singly spliced transcripts. This ribonucleoprotein (RNP) complex is then exported from the cell nucleus via interaction with cellular factors. For this purpose a C-terminally located leucine-rich sequence is necessary, which as a nuclear export sequence NES mediates the nuclear translocation of the Rev protein using cellular mechanisms (Pollard et al., 1998).

The reason why the late transcripts in the absence of Rev remain behind in the nucleus, which is a necessary precondition for the Rev dependence and thus the time-regulated expression of gag, pol and env, is still disputed. In principle there are two main alternative ideas about nuclear retention of late transcripts.

It is assumed that a cellular transcript can leave the cell nucleus only once the splicing process has been completed, and all active splicing sites have been removed from the primary transcript. Late viral transcripts are intron-containing, only incompletely spliced pre-mRNAs, which are transported to the cytoplasm with the aid of Rev and RRE. For this reason the influence of the cellular splicing machinery on the nuclear retention of the late transcripts was investigated early on (Mikaelian et al., 1996) (Kjems et al., 1991; Kjems et al., 1993; Chang et al., 1989; Powell et al., 1997; Lu et al., 1990; O'Reilly et al., 1995). Due to the presence of variously active splicing sites, the splicing process in HIV-1 transcripts appears to take place only sub-optimally. It has therefore been suggested by several groups of researchers that Rev permits the export of transcripts which can be retained within the splicing machinery due to the formation of inefficient splicing complexes.

On the other hand it has however been shown that the late HIV-1 genes, such as for example env, remain repressed in their expression also in the absence of active splicing sites, and therefore the influence of the splicing machinery appears to be more indirect (Nasioulas et al., 1994). For this reason so-called inhibitory sequences (INS) or cis-active repressor elements (CRS) within the reading frame have been postulated, which negatively influence the expression (Nasioulas et al., 1994; Olsen et al., 1992; Schwartz et al., 1992b; Maldarelli et al., 1991). These repressor sequences located within the coding mRNA do not however possess any common sequence motif, such as for example the AUUUA instability motif within the 3'-UTR of the unstable GM-CSF mRNA (Chen et al., 1995), but are notable only for their always high A/U content. Thus, the fusion of the postulated INS-containing fragments from reading frames of later genes (such as gag and env) to a CAT-reporter system resulted in a reduced reporter activity (Cochrane et al., 1991; Rosen et al., 1988). This reduction of the expression of gag and poi could to some extent be cancelled again by multiple quiet point mutations within the "wobble" positions (Schwartz et al., 1992a, Schneider et al., 1997). The unspliced and singly spliced HIV-1 mRNAs thus appear to contain cis-active repressor elements, which are removed either by multiple splicing or are overcome by an Rev/RRE-mediated nuclear export.

An elegant method of circumventing the Rev dependence of HIV transcripts has been developed by Schwartz and Schneider, as already mentioned, in the form of a partial change of the reading frame of HIV genes. A consequent development of this concept led to the synthesis of a codon-optimised HIV-gag-pol gene using synthetic oligonucleotides (Wagner et al., 2000; Graf et al., 2000). This type of matching of the G/C content and codon usage to that of mammalian cells permitted a constitutive synthesis of the Gag-Pol polyprotein in mammalian cells in large amounts. The basic mechanism of this decoupling of the protein synthesis from the Rev dependence is an altered nuclear export of the mRNA. Whereas the HIV wild-type RNA is involved in an alternative export pathway characterised by the Crm1 protein, depending on the HIV shuttle protein Rev, the synthetic mRNA on the regular nuclear export pathway for cellular mRNAs is transported constitutively into the cytoplasm. This constitutive expression of HIV proteins opens up new ways for an HIV treatment at the genetic level.

The publication by Graf et al. (2000) does not however disclose methods for a gene expression inducible with the aid of a transactive factor.

Just like the aforementioned publication by Graf et al., DE 1 053 781 A1 too is concerned with the RNA export from the cell nucleus into the cytoplasm. This patent application thus relates to making reporter genes dependent on Rev in order to be able to control the expression of the reporter gene via the nuclear export.

Since a Rev dependence and RRE dependence impose certain restrictions on the development of HIV-based vectors, Kotsopoulou et al. (2000) synthesised a codon-optimised HIV-1-gag-pol gene. This gene was introduced into a mammalian expression vector and investigated as regards the dependence on Rev. The authors did not however use any promoters inducible with the aid of transactive factors. A method according to the invention is accordingly not disclosed.

The expression of anti-HIV genes in cells can be efficiently used for an intracellular inhibition of HIV replication (Bunnell et al., 1998). In the meantime a whole range of HIV gene therapy strategies have been developed, ranging from antisense constructs and RNA decoys via specific RNA-decomposing ribozymes and RNA interference to transdominant-negative proteins derived from HIV. Apart from these intracellular inhibitors, which interfere in a targeted manner in steps in HIV replication, within the scope of a gene therapy the re-infection of cells or the propagation of descendant viruses can also be prevented. Various approaches are concerned with the expression of secretable anti-HIV proteins, immunostimulating or non-specific antiviral factors and, not least, with the expression of cell-toxic factors following infection (for overview see Mautino et al., 2002).

Apart from these rather non-specific inhibitory strategies, virus multiplication can take place by preventing virus release in a very specific manner, using HIV-own protein derivatives. Deletions in Gag mediate a transdominant-negative (TDN) effect to the new formation and release of descendant viruses (von Poblotzki et al., Trono et al., 1989; Smythe et al., 1994: Furuta et al., 1997). These deletions are in p17MA, in the transition region of p17MA/p24CA and in the C-terminal domain of p24CA. The exact action mechanism of the transdominant-negative effect has not been clarified. Some clues point however to an influence of the reduced cyclophilin A binding capacity of the mutated p24CA (Chiu et al., 2002) and to an altered membrane targeting, from the plasma membrane to the ER membrane, with deletions in p17MA (Facke et al., 1993; Gallina et al., 1994; Ono et al., 2004). Since Gag is a very strongly multimerising polyprotein and an exact clustering is necessary for the correct formation of HIV particles (Wilk et al., 2001), it is obvious that TDN Gag deletion derivatives with functional assembly domains (C-terminal domains of p24CA) directly interfere, by a binding to wild-type Gag proteins, with the assembly of HIV capsids and thus demonstrably lead to an inhibition of HIV replication.

Particularly the last strategy however exhibits some problems in a constitutive protein expression. Thus, the expression of the foreign gene can lead to cell toxicity, a faulty regulation of cellular functions, a reduced regulation of the transcription and, specifically in the case of a protein derived from HIV, to an undesirable immune response (Smythe et al., 1994). In order to circumvent these problems, various strategies are adopted to make the expression of the transgene dependent on an HIV infection.

In various approaches a Tat-, a Rev- and a Tat/Rev-dependent expression have been investigated and in some cases the inhibition of HIV replication in vitro has been described (Caruso et al., 1992; Harrison et al., 1992; Liu et al., 1994). In agreement with this, the expression of thymidine kinase (Marcello et al., 1998) and interferon $\alpha 2$ (Ragheb et al., 1999) could be raised by Tat by a factor of 5 and 4 respectively, and by Rev by a factor of 3.3 and <2 respectively. The combined addition of Tat and Rev led however to very different results: the expression of thymidine kinase was raised by a factor of 7, whereas for interferon $\alpha 2$ an increase in expression by a factor of >300 was reported. For HIV-1 TDN Gag derivatives a clear Rev-mediated induction of protein synthesis (with low basal activity) could be shown, which was associated with a broad inhibition of HIV replication (up to 94%) (Smythe et al., 1994; Furuta et al., 1997). For the combination of Tat-dependent and Rev-dependent expression of TDN Gag, a sharply increased protein synthesis was achieved by co-transfection of tat-expression and rev-expression plasmids (Ding et al., 2002; Cara et al., 1998). Here it was found however that the inhibition of the HIV replication was only partial (Cara et al., 1998) and reached a high level only by combination with various inhibitory strategies (Ding et al., 2002; Cara et al., 1998). In contrast to this the LTR/Tat-inducible expression of suicide genes such as TK led, in many cases to an inhibition of virus replication (Marcello et al., 1998; Miyaka et al., 2001; Ragheb et al., 1999).

As regards the basal activity, it has been correspondingly shown that a dependence on Rev does not lead to an absolute prevention of protein synthesis. Rev influences the export of RNA from the cell nucleus and is functional only in combination with corresponding cis-active retention sequences (INS, see above) and a cis-located recognition sequence (RRE). Gag genes isolated and reduced in size (and therefore also in the size of the INS) are efficiently transcribed under a correspondingly active promoter (e.g. CMV), and it is clear that a certain part of the RNA reaches the cytoplasm and is translated without the support of Rev.

There is no unambiguous data regarding the regulation by LTR/Tat. Most reports have described a basal activity of the genes under LTR control (Caruso et al., 1992; Ding et al., 2002; Muratori et al., 2002; Cara et al., 1998). Possible explanations of this expression in the absence of Tat are an activation of the LTR promoter by TNF$\alpha$, which was secreted from the corresponding transduced cells (Muratori et al., 2002), or elements of the vector construct, which are derived from HIV (Miyake et al., 2001).

Also, the length of the LTR that is used may have an influence on the regulation. Thus, a complete switching off of the transcription in the absence of Tat was detected with a minimal LTR (Miyake et al., 2001), i.e. a “tight” inducible promoter was described.

For an HIV-dependent transgene expression the LTR/Tat system therefore appears to be the more important switch module; and this also for the reason that an induction by Rev is downstream of that by Tat, which can lead to an initial virus multiplication, and specifically shortly before the inhibition by the transgene can act. Thus, among other things the observed incomplete inhibition of the replication after Rev induction is explained (Smythe et al., 1994).

However, for a Tat-inducible expression of transdominant-negative (TDN) Gag derivatives, in contrast to suicide genes up to now a sufficient inhibition of the HIV replication has still not been detected (see above). There are several possible explanations for this:

i) The TDN action correlates with the amount of the TDN protein, i.e. a certain limit must be exceeded in order to achieve an effective intervention. The amount of protein depends however to a large extent on the promoter activity. Compared to highly active viral promoters (e.g. CMV SV40) this is relatively slight in HIV-1 LTR, and is therefore possibly not sufficient.

ii) The TDN derivatives used hitherto are derived from the HIV-1 wild-type genome, and consequently contain INS motifs and are therefore dependent on a Rev-mediated nuclear export. As described above, the actual inhibitory action starts only with the presence of REV in the cell nucleus, whereby the first HIV transcripts pass unhindered into the cytoplasm and can complete the replication. It is therefore not surprising that a combination of both regulation systems leads to a very inefficient inhibition of HIV replication (Cara et al., 1998).

Apart from the LTR-tat system, many other inducible viral promoters are known. Also, other inducible expression systems are known in the prior art. Often however the desired degree of gene expression cannot be achieved with an inducible system. An object of the present invention is accordingly to provide a method for inducible gene expression.

This object is achieved by a method for inducible gene expression, comprising (i) provision of a target nucleic acid sequence to be expressed,
(ii) modification of the target nucleic acid sequence to be expressed so that an increase in the expression is achieved,
(iii) operative coupling of the modified target nucleic acid sequence with an inducible transcription control sequence,
(iv) expression of the modified target nucleic acid sequence in a suitable expression system by a transactive factor.

It has surprisingly been found that the inducible expression of a coded gene in a target nucleic acid sequence to be expressed (hereinafter also termed transgene) can be significantly improved if on the one hand its sequence at the nucleic acid level is modified to achieve an increase in gene expression, and on the other hand the target nucleic acid is expressed under the control of a transcription control sequence inducible by a transactive factor.

An inducible gene expression is essential for example when toxic gene products are used, and with other, therapeutically usable genes has decisive advantages compared to a constitutive expression:

- A non-infected cell is in its physiological performance not subjected to stress due to a high expression of additional factors.
- Non-specific or non-foreseeable interactions of the gene products could lead to physiological modifications such as activation, proliferation or the like, also in neighbouring cells, in tissues or in the whole organism.
- Proteins derived from HIV are recognised by immune cells in the environment of an HIV infection and the corresponding protein-expressing cells are eliminated.
- In the case of toxic factors a constitutive production must be avoided.

A transcription control sequence is a nucleic acid sequence which permits the expression of a nucleic acid sequence, in particular of a gene, operatively associated therewith. It may in this connection be a promoter, and in addition the transcription control sequence may also include further elements such as for example enhancers and the like. Preferably the inducible transcription control sequence is an inducible promoter. In this connection in principle every inducible promoter system that is known in the prior art is suitable. A natural or artificial inducible promoter, for example a promoter inducible by tetracyclin (Tet on/Tet off system), may for example be used. Furthermore, an inducible viral promoter may however also be used.

The transcription control sequence is induced by a transactive factor. The transactive factor is a factor that acts in trans and has an influence on the transcription. The transactive factor is preferably a transcription factor. Particularly preferably the transactive factor is a viral transactive factor.

Preferably the inducible transcription control sequence can be induced by a viral transactive factor. A viral inducible transcription control sequence that can be induced by a viral transactive factor may be derived from an arbitrary virus. Sequences of retroviruses, HCV (Hepatitis C Virus), HBV (Hepatitis B Virus), HSV (Herpes Simplex Virus), EBV (Epstein-Barr Virus), SV40 (Simian Virus 40), AAV (Adeno-associated Virus), Adenovirus, Papilloma Viruses or Ebola Virus are preferably used for this purpose. The transactive factors used in this connection are accordingly selected for example from the following viral factors, but are not restricted to these: NS5A (HCV), HB X (HBV), VP16/ICP4 (EBV), EBNA1/Rta (EBV), ART (HHV8), Large T-Antigen (SV40), Rep78/68 (AAV), E1A (Adenovirus), E2 (Papilloma Virus) and VP30 (Ebola Virus).

A retroviral LTR promoter or a functional partial sequence thereof is preferably used as inducible transcription control sequence that can be induced by a viral transactive factor. Preferably therefore the transactive factor is a retroviral Tat or Tax protein. The LTR promoter may be selected from LTRs of HIV-1, HIV-2, SIV, HTLV and other related retroviruses that contain LTR promoters. In particular lentiviral promoters are preferred, especially those of HIV.

A transactive factor within the meaning of the present invention is thus a factor which exerts in trans an influence on the transcription, preferably due to the fact that the transactive factor interacts with the inducible transcription control sequence. An example of such a transactive factor is thus the Tat protein already mentioned above.

In order to improve the gene expression the target nucleic acid sequence to be expressed is modified. This occurs at the nucleic acid level and preferably in such a way that the corresponding amino acid sequence is not, or is not substantially, altered. If the amino acid sequence is altered in the modification of the nucleic acid sequence in order to raise the gene expression, then this should have no influence on the function of the resulting protein.

The modification of the target nucleic acid sequence to raise the gene expression may be carried out in several ways.

On the one hand it is possible to match the codon usage of the transgene to the employed expression system. A eukaryotic expression system, in particular a mammalian-based one, is preferred, especially in this connection one based on mammalian cells, preferably human cells. The codon usage of the transgene is therefore preferably matched to the codon usage of mammalian cells, more preferably to that of human cells.

Modified target nucleic acid sequences according to the invention and preferably suitable for gene therapy can be created for example by choosing the codon distribution as it occurs in exported cellular mRNA. Preferably in this connection a codon choice should be used such as is most frequently or next most frequently employed in mammalian cells (Ausubel et al., 1994), and even more preferably the codon choice is matched to that of actively expressed mammalian genes. Preferably the nucleic acid sequence is modified for an optimal expression in mammals using the gene optimiser technology (German Patent Application DE 102 60 805.9, PCT/EP03/14850).

Instead of or also in addition to the matching of the codon choice, it is however also possible to optimise the GC content. This is preferably achieved by matching the GC content of the transgene as accurately as possible to the GC content of the expression system that is used. In this connection the degeneracy of the genetic code is preferably utilised, so that the alteration of the nucleic acid sequence for the purposes of increasing the GC content does not lead to an alteration of the amino acid sequence. The optimal percentage content of G and C nucleotides in a sequence to be expressed depends, as already mentioned, on the respective organism and on the respective cells in which the sequence is to be expressed. For example, the optimal GC content in nucleic acids in mammalian cells is about 50%. Reference documents already exist in which the person skilled in the art can look up the optimal GC content for various organisms and cells. The regularly updated codon usage database exists at the Kazusa DNA Research Institute, see also Nakamura, Y et al., (2000) Nucl. Acids Res. 28, 292. It is therefore no problem for the person skilled in the art to optimise, as regards the GC content, the nucleic acid sequence of the target nucleic acid to be expressed.

The optimisation of the GC content or the matching of the codon usage is preferably carried out by silent mutations or by mutations that do not influence the activity of the protein coded by the transgene. The codon usage need not necessarily be matched if the GC content of the said gene is already more than 50%. Genes with codon usage differing from the wild type may, as mentioned in the example, be produced from long oligonucleotides by a stepwise polymerase chain reaction (PCR).

A further possible way of modifying the target nucleic acid sequence to be expressed for the purposes of improving the expression is, either instead of the above possibilities, or in addition to these, to purposefully eliminate motifs that negatively influence the transcription. This includes for example the deletion of nucleic acid motifs such as poly-A sequences and the like, which could well already be known to the person skilled in the art. Further such motifs negatively influencing the expression include RNA instability motifs, adenine-rich motifs, recognition motifs for endonucleases, motifs that influence the RNA secondary structure, and the like.

The target nucleic acid sequence to be expressed preferably codes for a therapeutic and/or diagnostic protein. Such a protein may be chosen for example from toxic gene products, suicide factors, apoptosis-inducing proteins, messenger substances, transactive factors, regulator proteins, transdominant-negative proteins, cytokines, chemokines, etc. Specific examples are interferon α, SDF-I RANTES, MIP1α, TNF and interleukins, in particular interleukins 2, 6, 10, 12, 15 and 28. Preferably the target nucleic acid sequence to be expressed codes for a gene which, when the LTR/Tat system is used, produces proteins, for example after activation by HIV infection, which are capable of inducing the natural defence mechanisms of adjacent cells or of preventing, by binding to the corresponding receptors, an infection with HIV. In the case of HIV these are in particular the receptors CD4, CCR5 or CXCR4.

Further examples are enzymes, such as for example thymidine kinase, cytosine deaminase, purine nucleoside phosphorylase, carboxypeptidase, carboxylesterase, nitroreductase, peroxidase, xanthine-guanine phosphoribosyltransferase, glycosidase, thymidine phosphorylase and the like.

The method for the expression of toxic gene products, e.g. thymidine kinase from herpes viruses, nucleases or apoptosis-inducing proteins (e.g. FAS/FAS ligand, caspases, etc.) is particularly suitable. Apart from caspases, also suitable are TNF-related apoptosis-inducing ligand (TRAIL), protein kinase C (PKC), Tumor necrosis factor (TNF), apoptosis-inducing factor (AIF) and the like. After infection with HIV, the expression of genes would in this case be induced, the cells would be damaged, and thus the new production and propagation of descendant viruses would be prevented.

Furthermore, the transgene may be a regulator gene which, after its induced expression in a cell, acts as a molecular switch molecule and switches the expression of other genes on or off. A gene that codes for a transcription factor may for example be used as such a regulator gene. Of course, these possible uses are not restricted to infection with HIV, and the person skilled in the art is able to use corresponding systems also for other infections.

The transgene is preferably a viral gene.

Moreover, the target nucleic acid sequence to be expressed may also be a gene for a transdominant-negative (TDN) protein. Preferably in this case it is a viral TDN protein, preferably a retroviral TDN protein and most preferably a lentiviral TDN protein.

In this connection lentiviral TDN proteins are particularly suitable, e.g derivatives of $Pr55^{gag}$, Gp41, Gp120, Rev, protease, integrase, reverse transcriptase, Nef, Vpr, Vpv or any other lentivirus protein that is able to interrupt the replication cycle of lentiviruses, in particular HIV, or to prevent the release or splitting off of virus particles.

Preferably HIV-1 gag (group-specific antigen) is used as transgene, in which case its codon choice is adapted to the codon choice as is to be found in human genes.

Particularly preferably a gag gene is used that contains further deletions. This can further intensify the TDN action. Preferably in this case further deletions in the p24 region or individual or multiple assembly domains are involved.

For example, the amino acid sequence of the gag gene product was back-translated into a synthetic Gag-coding reading frame using the codon choice of human genes. This reading frame known as “syngag” was then constructed as a completely synthetic reading frame using long oligonucleotides and a stepwise PCR. The syngag reading frame was then cloned into an expression vector. The produced syngag vector appeared in the expression of HIV gag as being completely independent of the presence of the Rev protein, an RRE sequence, a 5' untranslated region (UTR) or splice sites. The output gag gene, which corresponds in its codon choice to the HIV-1 wild-type gene (wtgag), appeared in its expression however as dependent on Rev RRE and the 5'-UTR inclusive splicing donor (Graf et al., 2000).

Furthermore the invention therefore preferably relates to a method for the expression of transdominant-negative (TDN) lentivirus proteins in eukaryotic cells, comprising:

(a) Introducing a vector, comprising a target nucleic acid sequence to be expressed, which codes for a TDN lentivirus protein and whose codon usage is matched to that of mammals, and a promoter sequence inducible by lentivirus Tat protein in operative coupling with the target nucleic acid sequence, in a eukaryotic cell,
(b) Provision of the Tat protein so that an expression of the target nucleic acid sequence is induced.

Surprisingly the LTR/Tat system can be used despite the aforementioned limitation, if, as described above, the expression of the TDN derivative is independent of Rev/RRE. In the present invention this is achieved by matching the codon usage to that of mammalian cells.

In the combination of LTR and synthetic HIV reading frames an early expression of the TDN gene—in an early phase of HIV infection—is connected with an efficient nuclear export (plus an RNA stabilisation) and thus with a protein biosynthesis, before HIV-own structure proteins and thus target proteins are produced. Overall this combination offers i) a high TDN protein amount combined with ii) a kinetically favourable expression behaviour and iii) a very efficient inducibility.

As a delimitation with respect to the hitherto described methods, i) the inducibility of the expression is restricted to the presence of Tat, whereby the need for HIV RRE/Rev in the transfer construct is avoided, and ii) the Rev independence of the transcript is guaranteed by a suitable codon choice for the transfer construct.

The transcription control sequence for the transgene is preferably positioned similarly to the natural occurrence.

The induction of the promoter is carried out by a lentiviral Tat protein, preferably by the HIV Tat protein, which acts as transactive factor. This allows an induction of the promoter by an infection of the cell containing the vector, to take place with a lentivirus, in particular HIV, by itself. Such an in trans active factor is understood within the meaning of the present application to be an individual protein as well as a protein complex.

The stabilisation of the RNA and the improvement of the nuclear export properties as well as the independence of the protein production on an RRE/Rev interaction (in the case of HIV-derived proteins) may for example be achieved by a corresponding codon choice, taking into account motifs that influence RNA stability.

The invention moreover relates to a nucleic acid vector comprising:

(a) a target nucleic acid sequence to be expressed, (b) a transcription control sequence inducible by a transactive factor, preferably by a viral transactive factor, in operative combination with the target nucleic acid sequence to be expressed, wherein the sequence according to (a) is modified at the nucleic acid level in such a way that an increase in expression is achieved.

A nucleic acid vector is understood in this connection to denote a nucleic acid construct that is capable of expressing a target nucleic acid sequence contained thereon in a suitable expression system, e.g. a cell, an organism or in an in vitro system, and which includes at least one target nucleic acid sequence to be expressed and an inducible transcription control sequence in operative combination therewith. Such a vector may contain further coding sequences, such as e.g. selection marker genes and the like. The person skilled in the art is able to use the target nucleic acid sequence to be expressed in combination with its transcription control sequence in a suitable commercially obtainable plasmid vector or the like or also a self-constructed vector.

The target nucleic acid sequence to be expressed and the inducible transcription control sequence may also be chosen in this case as described above. Also, the modification of the sequence may be carried out as explained above.

A preferred embodiment relates to vectors which can be used in HIV gene therapy and which are characterised in that they code for a therapeutic gene that is expressed only after infection of the cell by HIV. The transcription of corresponding genes is in this connection controlled by the HIV-own LTR (long terminal repeat) region and takes place in the presence of the HIV-Tat protein. Also, preferably synthetic reading frames adapted to expression in human genes are used for the therapeutic genes, to increase the gene expression, in particular the RNA stability and the RNA nuclear export. These genes may preferably be targeted against different steps in the HIV replication cycle and intervene in the infection of cells, the replication of HIV or the propagation of descendant viruses.

The vector according to the invention may additionally contain a further transgene, which preferably codes for a therapeutic, gene therapeutic and/or diagnostic protein. This further transgene may likewise be under the control of an LTR promoter, for example the same promoter as the sequence according to (a). However, it may also be controlled by a separate promoter, which may be constitutive or inducible.

The vector may for example be of viral (e.g. adeno-associated viruses, adenoviruses, retroviruses, herpes viruses, alpha viruses, etc. a) or bacterial origin, or may be a plasmid. Particularly preferably the inducible transcription control sequence is chosen so that the expression of the foreign gene depends on the presence of the HIV-1 Tat protein. If the Tat transactivation is successfully reconstituted, there should preferably be a measurable increase in the expression of the Tat-dependent gene by a factor of at least 3, preferably 5, and still more preferably by a factor of 10 or more.

The vector preferably contains a sequence according to SEQ ID NO. 1, 16 or 17.

The present invention furthermore provides modified target nucleic acid sequences which, when operatively coupled with a suitable inducible transcription control sequence, bring about an increased gene expression. Preferably these modified target nucleic acid sequences are selected from the sequences given in the examples of the present invention and specified in the sequence protocol. Most preferred are the modified target nucleic acid sequences selected from the following sequences: SEQ ID NO. 1, 16 and 17.

The present invention furthermore provides cells, preferably eukaryotic cells, more preferably mammalian cells, most particularly preferably human cells, which have been transformed with a nucleic acid or a vector, as described above, in which the nucleic acid is present in a transcriptable form. The nucleic acid and the vector may for example be present episomally or may be stably integrated into the chromosome. In this case the cell may contain one or more copies.

The present invention moreover relates to medicaments based on the vectors and modified lentiviruses and cells disclosed here. The medicaments according to the invention are suitable for therapeutic and diagnostic uses, and in particular are suitable for the diagnosis, prevention or treatment of virus-associated diseases and/or tumours. For these applications the target nucleic acid sequence to be expressed may for example in particular be a suicide gene or the like.

The medicaments may for example be used for treatment purposes, preferably for the treatment of lentiviral infections, e.g. HIV and SIV, in particular HIV-1 and HIV-2. The person skilled in the art is able to match the promoter sequence to the system in which the expression is to take place. Lentiviral infections can now be controlled in this way, by treating infected persons in vitro, ex vivo and of course in vivo, for example by introducing the nucleic acids or vectors according to the invention into PMLs from these patients or into T cells in different stages of differentiation, or into stem cells.

The invention will be described in more detail hereinafter with the aid of the following figures and examples.

FIGURES AND SEQUENCES

FIG. 2A shows an HIV-1 p24-specific western blot of transfected cells.

FIG. 2B shows a p24 ELISA test.

FIG. 3A shows an HIV-1 p24-specific western blot of transfected cells.

FIG. 3B shows an ELISA test.

FIG. 4A shows the inhibition of the release of particles in percent according to a p24 ELISA test.

FIG. 4B shows the inhibition of the infectivity of the released virus particles in percent.

FIG. 5A shows the inhibition of the release in percent.

FIG. 5B shows the inhibition of infectivity in percent.

FIG. 6 shows the sequences of TDsyngag and TDwtgag as well as a sequence comparison between TDwtgag and TDsyngag.

FIG. 7 shows the nucleic acid sequences of TDsyngag delta 2 and TDsyngag delta 2 delta p7.

Figure 1:
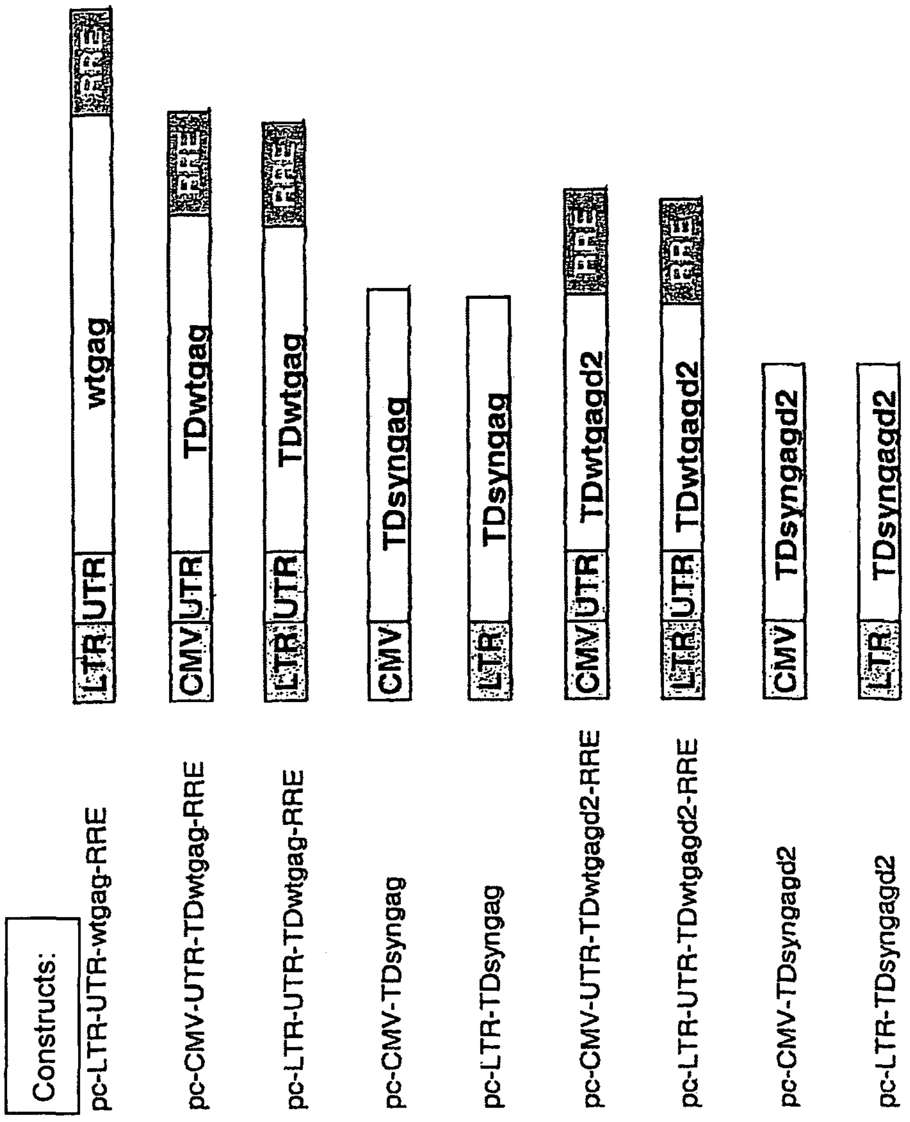
FIG. 1 shows diagrammatically all produced gag-coding constructs.

SEQ ID No. 1 shows the nucleic acid sequence of TDsyngag.

SEQ ID No. 2 shows the amino acid sequence of TDsyngag.

SEQ ID No. 3 shows the nucleic acid sequence of TDwtgag.

SEQ ID No. 4 shows the amino acid sequence of TDwtgag.

SEQ ID Nos. 5 to 15 show various oligonucleotides.

SEQ ID No. 16 shows the nucleic acid sequence of TDsyngag delta 2.

SEQ ID No. 17 shows the amino acid sequence of TDsyngag delta 2.

SEQ ID No. 18 shows the nucleic acid sequence of TDsyngag delta 2 delta p7.

SEQ ID No. 19 shows the amino acid sequence of TDsyngag delta 2 delta p7.

EXAMPLES

Example 1

Production of Independent Tat-Dependent, Rev-Dependent and Tat- and Rev-Dependent Gag Gene Derivatives HIV-1 transdominant-negative (TDN) gag derivatives were produced as constitutively, Tat-, Rev- or Tat/Rev-dependent expressing gene constructs. The Rev dependence was achieved by using HIV wild-type (wt) gene sequences, including the 5'-untranslated region (UTR), in conjunction with the HIV Rev-responsive element (RRE). The Rev-independence was made possible by synthetic, GC-rich gene sequences, in which the coded amino acid sequence is identical for both constructs. A dependence on Tat was achieved by using HIV-1 LTR as transcription control. On the other hand, the CMV-promoter/enhancer was used for a constitutive transcription. By appropriate combination of the elements a constitutive expression (CMV-syngag), a Tat-dependent (LTR-syngag), a Rev-dependent (CMV-UTR-wtgag-RRE) and a Tat- and Rev-dependent (LTR-UTR-wtgag-RRE) expression of identical (at the protein level) TDN gag derivatives was generated.

The reading frame of the HIV-1 group-specific antigen (gag) (GenBank Accession Number: M15654.1 HIVBH102, nucleotides 112-1650; Reference: Ratner L, Haseltine W, Patarca R, Livak K J, Starcich B, Josephs S F, Doran E R, Rafalski J A, Whitehorn E A, Baumeister K, et al., Complete nucleotide sequence of the AIDS virus, HTLV-III. Nature. 1985 Jan. 24-30; 313 (6000): 277-84) should be constructed artificially using a codon choice, such as is to be found in human cells. For this purpose the amino acid sequence of the Gag protein (corresponding to GenBank Accession Number: M15654 JIVBH102, nucleotides 112-1408) with a deletion of nt 304-489 was converted into a corresponding nucleotide sequence. A corresponding software package (GeneOptimizer) was used for the codon optimisation and optimisation of the RNA sequence. For the sub-cloning as well as for the attachment of further sequence elements within untranslated regions, further restriction interfaces were inserted. The nucleotide sequence, including the interfaces, is given in SEQ ID NO. 1.

This sequence was produced as a fully synthetic gene using synthetic oligonucleotides according to an already described method (Zolotukhin et al., 1996).

A comparison of the nucleic acid sequences of TDsyngag (codon choice derived from mammalian genes) and TDwtgag (codon choice derived from HIV structure genes) is shown in FIG. 6. The TDgag-coding DNA fragment ("TDsyngag") produced in this way was inserted into the expression vector pcDNA3.1(+) (Invitrogen) using the interfaces EcoRI and Xho I, under the transcriptional control of the cytomegalovirus (CMV) early promoter/enhancer ("pc-CMV-TDsyngag").

To produce a similar expression plasmid, though corresponding in its codon choice to the HIV wild-type, the coding region of HIV-1 gag, including the 5'-untranslated region (UTR), was subcloned and, in order to meet the conditions for a Rev-mediated nuclear export, an RNA target sequence (RRE) was attached to the wtgag-coding region (Graf et al., 2000). This target sequence interacts at the RNA level with a viral nuclear export protein (in the case of HIV-1 the Rev protein) and cellular nuclear export proteins.

In order to ensure a matching at the protein level, the wild-type construct was C-terminally shorted by introducing two successive stop codons in the gag reading frame (codons for 372F and 373L were mutated). The mutations were introduced by directed mutagenesis (QuickChange site-directed mutagenesis kit, Stratagene) using the oligonucleotides gag-stop1 and gag-stop2. The resulting construct was designated pc-CMV-UTR-wtgag-RRE. Using the oligonucleotides Del1 and Del2, a deletion from nt 304 to nt 489 was introduced into this construct, similarly to the TDsyngag (pc-UTR-TDwt-gag-RRE). The coding sequence is given in SEQ ID No. 3.

The coding sequences were placed under the transcriptional control of the HIV promoter, in order to achieve a Tat dependence of the gag protein derivative. The HIV-1 long terminal repeat (LTR) contains such a promoter. This region was amplified by means of PCR using the oligonucleotides ltr1 and ltr2 from proviral HIV-1 DNA (HX10, see (Ratner et al., 1987)) and cloned using the interfaces MluI and EcoRI directly 5' in front of the ATG of the gag-coding reading frame in pc-CMV-TDsyngag, the CMV promoter having been replaced by the LTR. For the replacement of the promoter in the wt gag construct, parts of the HIV genome were amplified using the oligonucleotides ltr1 and ltr3 in a PCR reaction and replaced using the interfaces MluI and CiaI of the CMR promoter in the pc-CMR-UTR-TDwtgag-RRE construct. At the same time the natural reading frame of the HIV provirus (with the sequence LTR, UTR, gag) was produced again. The resulting constructs have been denoted hereinafter "pc-LTR-TDsyntgag" and "pc-LTR-UTR-TDwtgag-RRE".

All produced Gag-coding constructs are shown diagrammatically in FIG. 1.

Example 2

The Expression of the TDgag Constructs can be Controlled by HIV Regulator Proteins All cell culture products were obtained from Life Technologies (Karlsruhe). All mammalian cell lines were cultured at 37° C. and 5% $CO_2$. The human lung cancer cell line H1299 was cultured in Dulbecco's modified eagle medium (DMEM) with L-glutamine, D-glucose (4.5 mg/ml), sodium pyruvate, 10% inactivated foetal bovine serum, penicillin (100 U/ml) and streptomycin (100 µg/ml). The cells were sub-cultured in a ratio of 1:10 after confluence was achieved.

$1 \times 10^6$ cells were seeded out in Petri dishes (diameter 100 mm) and transfected 24 hours later by calcium phosphate co-precipitation (Graham et al., 1973) with 30 µg TDgag plasmids and 15 µg pc-tat (Tat expression plasmid) or pc-rev (Rev-expression plasmid) or pcDNA 3.1 vector (reference plasmid). With co-transfections of gag, tat and rev, 15 µg of plasmid were used for each one. Cells and culture supernatants were harvested 48 hours after transfection. The transfected cells were washed twice with ice-cold PBS (10 mM $Na_2HPO_4$, 1.8 mM $KH_2PO_4$, 137 Mm NaCl, 2.7 mM KCl), scraped off in ice-cold PBS, centrifuged for 10 minutes at 300 G and lysed for 30 minutes in lysis buffer on ice (50 mM Tris-HCl, pH 8.0, 0.5% Triton X-100 (w/v)). Insoluble constituents of the cell lysate were centrifuged off for 30 minutes at 10000 G and 4° C. The total amount of protein in the supernatant was measured with the Bio-Rad protein assay (Bio-Rad, Munich) according to the manufacturer's instructions.

An equal volume of double sample buffer (Laemmli, 1970) was added to the samples and heated for 5 minutes at 95° C. 50 µg of total protein from cell lysates were separated via a 12.5% SDS/polyacrylamide gel (Laemmli, 1970), electrotransferred onto a nitrocellulose membrane and analysed with the monoclonal $p^{24}$-specific antibody 13-5 (Wolf et al., 1990) and detected by means of a secondary, AP- (alkaline phosphatase) coupled antibody and identified by means of chromogenic colouration (FIG. 2*a*).

In addition to this the cell lysates were quantified in a commercially obtainable p24 ELISA test (NEN). 1 µg portions of the cell lysate were evaluated according to the manufacturer's instructions and the total concentration of HIV-1 p24 was determined (FIG. 2B).

Figure 2:
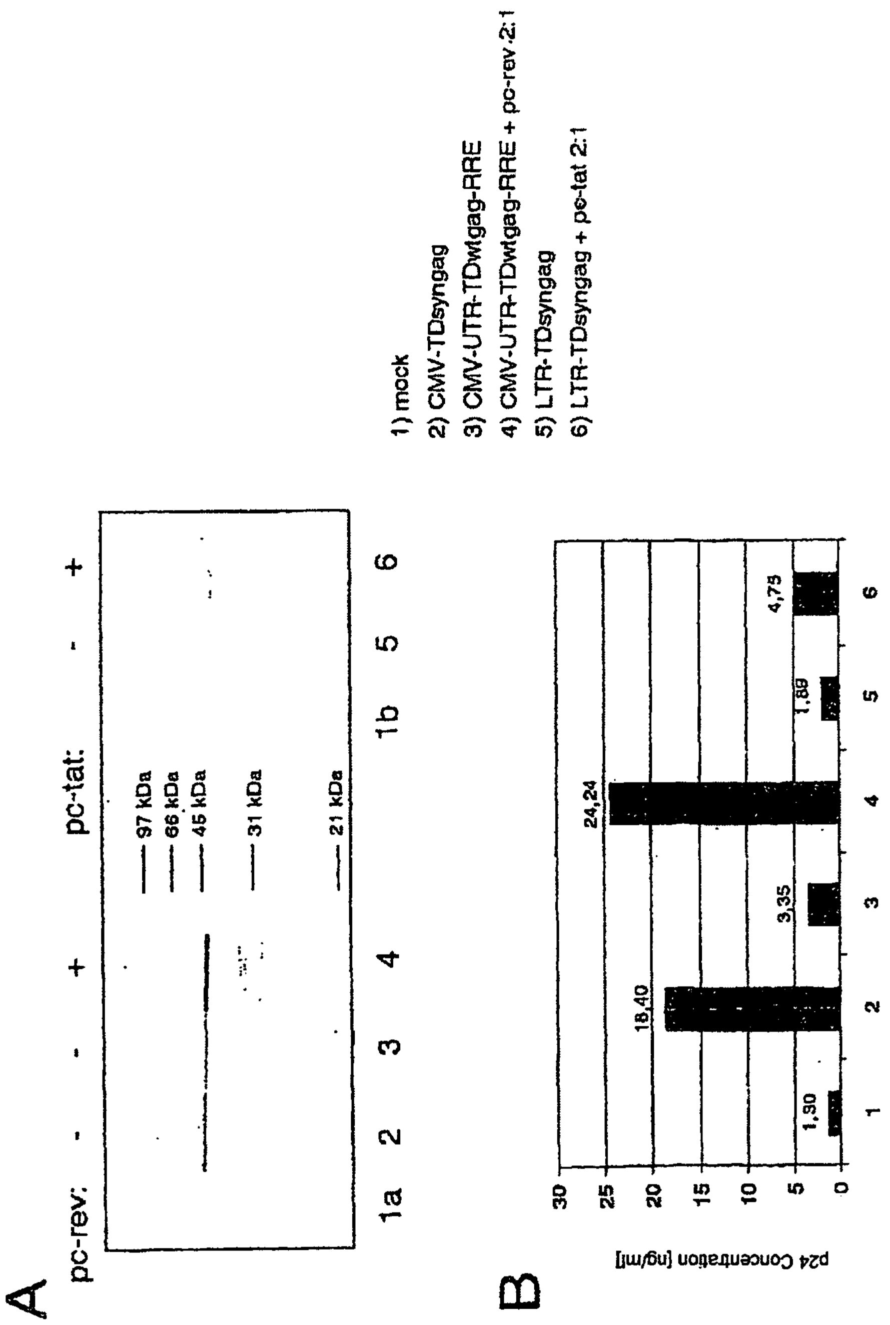
FIG. 2 shows the results of the expression of various gag-coding constructs in H1299 cells.
Figure 3:
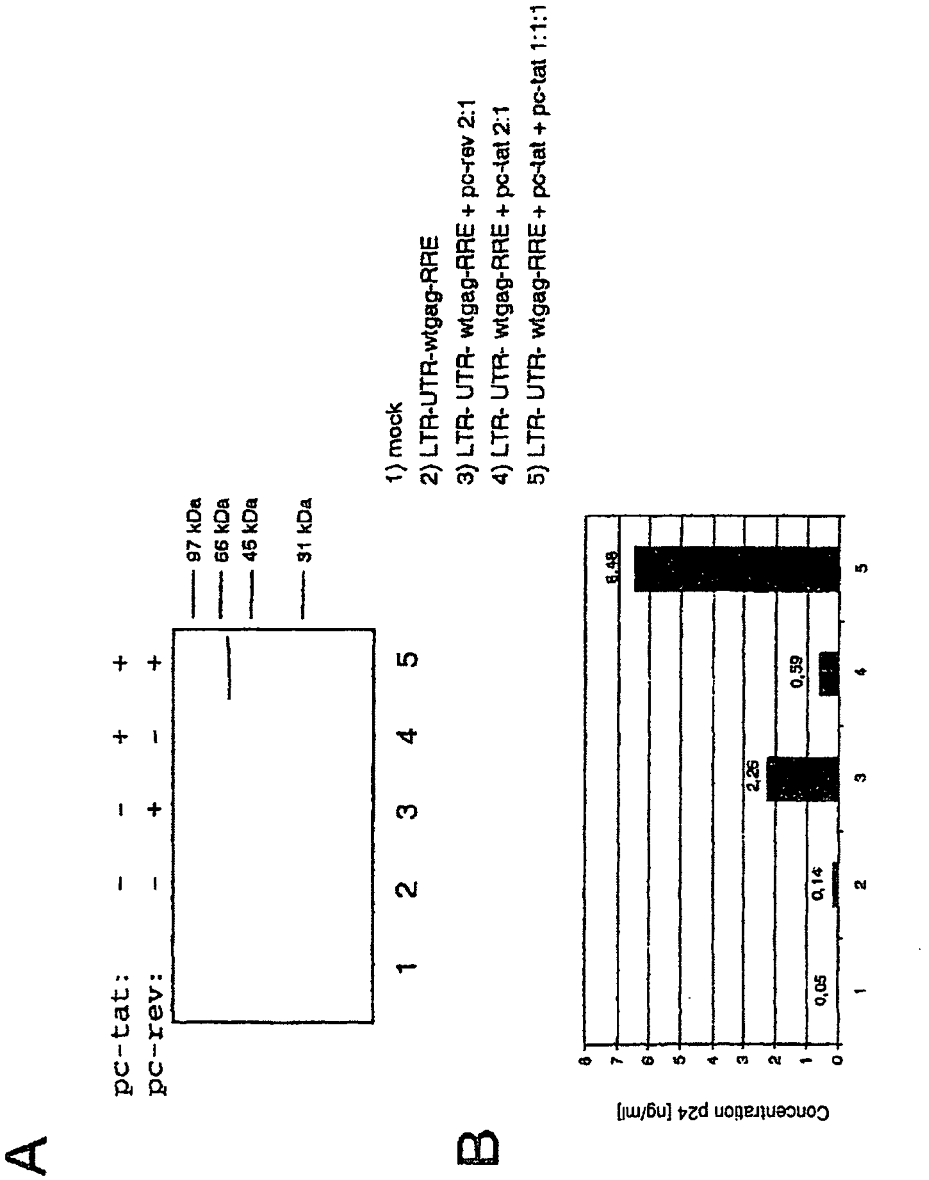
FIG. 3 shows the results of the expression of wild-type gag-expressing constructs in the presence and absence of Tat and/or Rev.

H1299 cells were transiently fixed with the gag constructs. The achieved expression was analysed in the presence and absence of Tat or Rev (FIG. 2). For the pc-CMV-TDsyngag a constitutive expression of TDgag was detected independently of Tat or Rev (FIGS. 2A, trace 2, and 2B, 2). The expression of TDgag could be raised for the pc-CMV-UTR-TDwtgag-RRE construct by Rev by a factor of 7 (FIG. 2A, traces 3 and 4 and 2B, traces 3 and 4), and for the pc-LTR-TDsyngag construct by co-transfection of pc-tat, by a factor of 2.5 (FIG. 2A, traces 5 and 6, and 2B, traces 5 and 6). The basal activity of the Tgag expression was somewhat lower for the pc-LTR-TDsyngag construct compared to pc-CMV-UTR-TDwtgag-RRE, for both constructs however was significantly reduced compared to pc-CMV-TDsyngag, and was only slightly above the negative control (ca. by a factor of 2.5 for pc-CMV-UTR-TDwtgag-RRE and 1.5 for pc-LTR-TDsyngag; FIG. 2B). The gene product of pc-LTR-UTR-TDwtgag-RRE could not be detected by these methods. The deletion in Gag leads to a reduced recognition by the monoclonal antibody, and in combination with a greatly restricted expression the TDgag amounts that are achieved are insufficient for a detection by antibodies. Accordingly, the Tat and Rev dependence was investigated in a reference construct (complete wtgag sequence). This construct (pc-LTR-UTR-wtgag-RRE) was dependent on Tat as well as on Rev. Tat alone led to an increase in expression by a factor of 4, Rev alone led to an increase by a factor of 16, and the combination of Tat and Rev by a factor of 47 (FIG. 3).

Example 3

The TDgag Constructs have a Transdominant Negative Effect on the HIV Particle Release H1299 cells were transiently transfected with combinations of plasmids, as described in Example 1. For a transfection, 15 µg of HX10 proviral DNA and 30 µg of the TDgag constructs or 30 µg of pcDNA3.1 were used as control for an uninhibited replication. After 48 hours the cell culture supernatants were harvested, cell constituents were sedimented by centrifugation (10 minutes at 10000 G) and the supernatants were incubated for 15 minutes at RT with 10% of a Triton x 100 solution (5%) to lyse the HIV particles in the supernatant. The treated supernatants were used in corresponding dilutions in a p24 ELISA test (NEN) and the p24 amount was quantified. The reduction of the p24 amount correlates directly with an inhibition of the particle release after transfection with an HIV provirus. The determined p24 amounts were compared to the control (co-transfection with pcDNA3.1, uninhibited) and the percentage (%) inhibition was calculated. At least 6 independent batches were tested for each combination.

Figure 4:
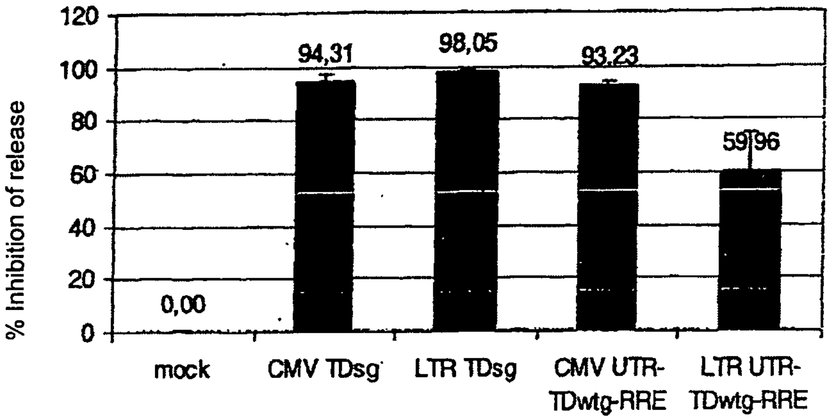
FIG. 4 shows the effect of the transdominant negative gag proteins on the release of HIV particles.
Figure 4:
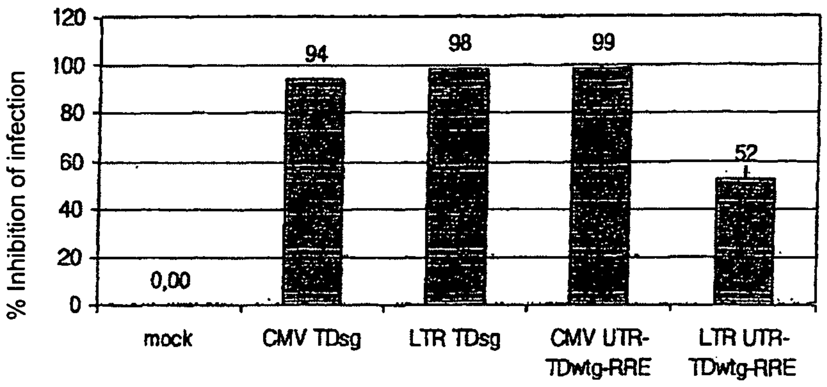

As can be seen from FIG. 4A, all tested TDgag constructs have led to a considerable inhibition of the particle release. The TDsyngag (TDsg) constructs exerted a very high inhibition independently of the upstream promoter. The inhibitory action of the TDwtgag (TDwtg) constructs depended however on the promoter region. The inhibition of the particle release was significantly higher under a CMV promoter control than under the HIV LTR promoter.

Example 4

The TDgag Constructs have a Transdominant Negative Effect on HIV Infectivity

H1299 cells were transfected with plasmid combinations as described in Example 3, and after 48 hours the supernatants were harvested and purified. In order to check the influence of the TDgag constructs on the release of infectious descendant viruses, the conditioned cell culture supernatants were tested in a corresponding indicator cell line (MAGI) (Kimpton et al., 1992).

Eukaryotic MAGI (multinuclear activation of a galactosidase indicator) cells are an indicator cell line that contains a reporter gene cassette which can be induced by HIV infection. The MAGI cells were made available by the UK Medical Research Council (MRC). In this cassette the viral LTR (long terminal repeat) promoter is upstream of the *E. coli* β-galactosidase gene (lacZ). The expression of lacZ accordingly depends on the transcription activity of the LTR promoter by the viral Tat.

For the infection, $3\times10^4$ cells per 300 µl of medium (in 48-well plates) were seeded out the previous day. After harvesting the transfected H1299 cell supernatants the Magi cells were infected with 100 µl of supernatant per batch and cultured for 48 hours.

To evaluate the infectivity, the medium was suctioned off and the wells were washed with PBS. The monolayers were fixed with 200 µl of fixing solution (1% formaldehyde, 0.2% glutaraldehyde in PBS) and after incubation for 5 minutes at room temperature were washed once again with PBS. 200 µl of staining solution (16 mg X-Gal in 4 ml DMSO, plus 40 ml PBS; addition of 400 µl K ferricyanide (400 mM), 400 µl K ferrocyanide (400 mM) and 8 µl $MgCl_2$ (1 M)) were then added to the cells. Incubation was carried out at 37° C. for between 15 minutes and 3 hours. The blue cells were counted in a light microscope.

The inhibition was measured as the reduction of blue cells and was given in terms of the number of blue cells in the positive control as % inhibition of the infectivity. The results correlate substantially with the data for the inhibition of the particle release (FIG. 4B). A virtually complete inhibition was found for the constructs pc-CMV-TDsyngag, pc-LTR-TDsyngag and pc-CMV-UTR-TDwtgag-RRE, whereas the construct pc-LTR-UTR-TDwtgag-RRE produced an about 50% inhibition (the results of an exemplary experiment from two independent batches are shown in FIG. 4B).

Example 5

Transdominantly Negative Effect of Tat-Dependent TDgag Derivatives with a Further Deletion in p24

Starting from the constructs pc-CMV-TDsyngag, pc-LTR-TDsyngag, pc-CMR-UTR-TDwtgag-RRE and pc-LTR-UTR-TDwtgag-RRE a further deletion was introduced into the gag reading frame by using the oligonucleotides Del3 and Del4 (syngag) and Del5 and Del6 (wtgag). This deletion concerns the amino acids 230 to 300, a region in which very many CTL epitopes have been identified. The expression of the corresponding TDN Gag-derivative after transfection of H1299 cells with the newly formed constructs pc-CMV-TDsyngagd2, pc-LTR-TDsyngagd2, pc-CMV-UTR-TDwtgagd2-RRE and pc-LTR-UTR-TDwtgagd2-RRE (schematic survey, see FIG. 1) could not be detected, since the modifications influence the affinity of the available gag-specific antibodies and could not be detected either in the western blot or in the p24 ELISA specific signals.

Figure 5:
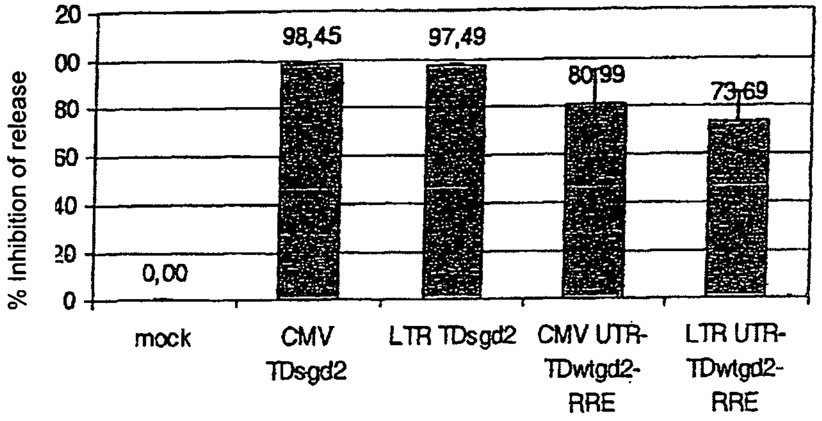
FIG. 5 shows the inhibition of the release of virus particles in percent, which were formed in the presence of transdominant negative gag constructs with further deletions in p24.
Figure 5:
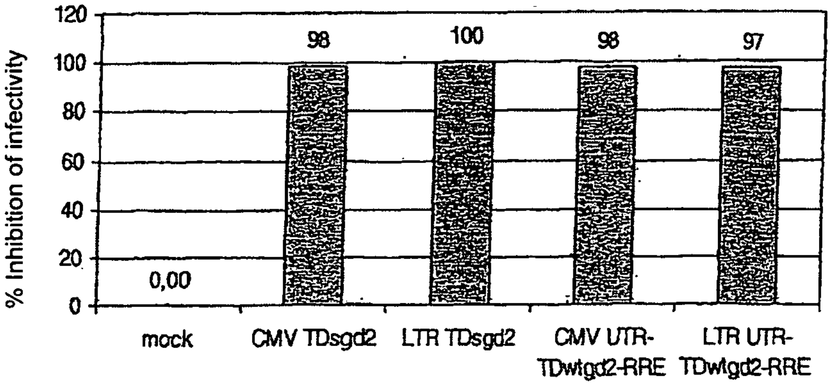

As described in Example 3, H1299 cells were transfected with combinations of HX10 (15 µg) and TDsyngagd2 or pcDNA3.1 (in each case 30 µg plasmid DNA) to check the TDN effect, and the supernatants were evaluated in the p24 ELISA test as described in Example 3, and by means of the MAGI cells as described in Example 4. An inhibition of the particle release (results of the p24 ELISA evaluation, FIG. 5A, at least 6 independent batches) and the infectivity of descendant viruses (results of the MAGI evaluation, FIG. 5B, two independent batches) was found for all used constructs. The order of the inhibitory effect (particle release) is in this case pc-CMV-TDsyngagd2 (98.45%) >pc-LTR-TDsyngag2 (97.49%) >pc-CMV-UTR-TDwtgagd2-RRE (80.99%) >pc-LTR-UTR-TDwtgagd2-RRE (73.69%) and thus corresponds substantially to the results of the TDgag experiments. Here the synthetic reading frames are also obviously superior as regards the inhibition of the particle release. The reduction of infectious descendant viruses was however comparable in this experimental batch (FIG. 5B). The combination LTR with synthetic reading frame showed clear advantages in a direct comparison of the Rev dependence to the Tat dependence.

TABLE 1

Employed oligonucleotide.

| Identification | Sequence 5'-3' | SEQ ID NO. |
|---|---|---|
| Del1 | TAAAGCTTCCTTGGTGTC | 5 |
| Del2 | TTCAGCCCAGAAGTAATACC | 6 |
| Del3 | TACAAGACCCTGCGCGCCGAGCAGGCC | 7 |
| Del4 | CTCCCTCATCTGGCCGGGGGCGATGGG | 8 |
| Del5 | TTCTCTCATCTGGCCTGGTGCAATAGG | 9 |
| Del6 | TATAAAACTCTAAGAGCCGAGCAAGCT | 10 |
| Gag-stop1 | GGAAGGCCAGATCTTCCCTCATTAATTAGCCTGTCTCTCAGTAC | 11 |
| Gag-stop2 | GTACTGAGAGACAGGCTAATTAATGAGGGAAGATCTGCCTTCC | 12 |
| Itr1 | ATTGTCGACACGCGTTGGAAGGGCTAATTCACTCC | 13 |
| Itr2 | ATTGAATTCCTCTCTCCTTCTAGCCTC | 14 |
| Itr3 | GCTTGCCCATACTATATG | 15 |

Bibliography

Ausubel, F. M., Brent, R., Kingston, R. E., Moore, D. D., Seidman, J. G., Smith, J. A. und Struhl, K. (1994) Percentage of Codon Synonomous Usage and Frequency of Codon Occurrence in Various Organisms, Current Protocols in Molecular Biology 2, A1.8-A1.9

Bunnell, B. A. und Morgan, R. A. (1998) Gene therapy for infectious diseases, Clin. Microbiol. Rev. 11, 42-56

Cara, A., Rybak, S. M., Newton, D. L., Crowley, R., Rottschafer, S. E., Reitz, M. S., Jr. und Gusella, G. L. (1998) Inhibition of HIV-1 replication by combined expression of gag dominant negative mutant and a human ribonuclease in a tightly controlled HIV-1 inducible vector, Gene Ther. 5, 65-75

Caruso, M. und Klatzmann, D. (1992) Selective killing of CD4+ cells harboring a human immunodeficiency virus-inducible suicide gene prevents viral spread in an infected cell population, Proc. Natl. Acad. Sci. USA 89, 182-186

Chang, D. D. und Sharp, P. A. (1989) Regulation by HIV Rev depends upon recognition of splice sites, Cell 59, 789-795

Chen, C. Y., Xu, N. und Shyu, A. B. (1995) mRNA decay mediated by two distinct AU-rich elements from c-fos and granulocyte-macrophage colony-stimulating factor transcripts: different deadenylation kinetics and uncoupling from translation, Mol. Cell Biol. 15, 5777-5788

Chiu, H. C., Wang, F. D., Yao, S. Y. und Wang, C. T. (2002) Effects of gag mutations on human immunodeficiency virus type 1 particle assembly, processing, and cyclophilin A incorporation, J. Med. Virol. 68, 156-163

Cochrane, A. W., Jones, K. S., Beidas, S., Dillon, P. J., Skalka, A. M. und Rosen, C. A. (1991) Identification and characterization of intragenic sequences which repress human immunodeficiency virus structural gene expression, .J. Virol. 65, 5305-5313

Ding, S. F., Lombardi, R., Nazari, R. und Joshi, S. (2002) A combination anti-HIV-1 gene therapy approach using a single transcription unit that expresses antisense, decoy, and sense RNAs, and trans-dominant negative mutant Gag and Env proteins, Front Biosci. 7, a15-a28

Facke, M., Janetzko, A., Shoeman, R. L. und Krausslich, H. G. (1993) A large deletion in the matrix domain of the human immunodeficiency virus gag gene redirects virus particle assembly from the plasma membrane to the endoplasmic reticulum, .J. Virol. 67, 4972-4980

Furuta, R. A., Shimano, R., Ogasawara, T., Inubushi, R., Amano, K., Akari, H., Hatanaka, M., Kawamura, M. und Adachi, A. (1997) HIV-1 capsid mutants inhibit the replication of wild-type virus at both early and late infection phases, FEBS Lett. 415, 231-234

Gallina, A., Mantoan, G., Rindi, G. und Milanesi, G. (1994) Influence of MA internal sequences, but not of the myristylated N-terminus sequence, on the budding site of HIV-1 Gag protein, Biochem. Biophys. Res. Commun. 204, 1031-1038

Graf, M., Bojak, A., Demi, L., Bieler, K., Wolf, H. und Wagner, R. (2000) Concerted action of multiple cis-acting sequences is required for rev dependence of late human immunodeficiency virus type 1 gene expression [In Process Citation], J. Virol. 74, 10822-10826

Graham, F. L. und van der Eb, A. J. (1973) Transformation of rat cells by DNA of human adenovirus 5, Virology 54, 536-539

Harrison, G. S., Long, C. J., Maxwell, F., Glode, L. M. und Maxwell, I. H. (1992) Inhibition of HIV production in cells containing an integrated, HIV-regulated diphtheria toxin A chain gene, .AIDS Res. Hum. Retroviruses 8, 39-45

Kimpton, J. und Emerman, M. (1992) Detection of replication-competent and pseudotyped human immunodeficiency virus with a sensitive cell line on the basis of activation of an integrated beta-galactosidase gene, J. Virol. 66, 2232-2239

Kjems, J., Brown, M., Chang, D. D. und Sharp, P. A. (1991) Structural analysis of the interaction between the human immunodeficiency virus Rev protein and the Rev response element, Proc. Natl. Acad. Sci. USA 88, 683-687

Kjems, J. und Sharp, P. A (1993) The basic domain of Rev from human immunodeficiency virus type 1 specifically blocks the entry of U4/U6.U5 small nuclear ribonucleoprotein in spliceosome assembly, J. Virol. 67, 4769-4776

Kotsopoulou E., Kim V. N., Kingsman A. J., Kingsman S. M., Mitrophanous K. A. (2000) A Rev-Independent Human Immunodeficiency Virus Type (1) (HIV-1)-Based Vector That Exploits a Condon-Optimized HIV-1 gag-pol Gene, J. Viral. 74, Nr. 10, 4839-4852

Laemmli, U. K. (1970) Cleavage of structural proteins during the assembly of the head of bacteriophage T4, .Nature 227, 680-685

Liu, J., Woffendin, C., Yang, Z. Y. und Nabel, G. J. (1994) Regulated expression of a dominant negative form of Rev improves resistance to HIV replication in T cells, Gene Ther 1, 32-37

Lu, X. B., Heimer, J., Rekosh, D. und Hammarskjold, M. L. (1990) U1 small nuclear RNA plays a direct role in the formation of a rev-regulated human immunodeficiency virus env mRNA that remains unspliced, Proc. Natl. Acad. Sci. USA 87, 7598-7602

Maldarelli, F., Martin, M. A. und Strebel, K. (1991) Identification of posttanscriptionally active inhibitory sequences in human immunodeficiency virus type 1 RNA: novel level of gene regulation, J. Virol. 65, 5732-5743

Marcello, A. und Giaretta, I. (1998) Inducible expression of herpes simplex virus thymidine kinase from a bicistronic HIV1 vector, Res. Virol. 149, 419-431

Mautino, M. R. und Morgan, R. A. (2002) Gene therapy of HIV-1 infection using lentiviral vectors expressing anti-HIV-1 genes, AIDS Patient. Care STDS. 16, 11-26

Mikaelian, I., Krieg, M., Gait, M. J. und Kam, J. (1996) Interactions of INS (CRS) elements and the splicing machinery regulate the production of Rev-responsive mRNAs, J. Mol. Biol. 257, 246-264

Miyake, K., Iijima, O., Suzuki, N., Matsukura, M. und Shimada, T. (2001) Selective killing of human immunodeficiency virus-infected cells by targeted gene transfer and inducible gene expression using a recombinant human immunodeficiency virus vector, Hum. Gene Ther. 12, 227-233

Muratori, C., Schiavoni, I., Melucci-Vigo, G., Olivetta, E., Santarcangelo, A. C., Pugliese, K., Verani, P. und Federico, M. (2002) Inducible expression of the deltaNGFr/F12Nef fusion protein as a new tool for anti-human immunodeficiency virus type 1 gene therapy, Hum. Gene Ther. 13, 1751-1766

Nasioulas, G., Zolotukhin, A. S., Tabemero, C., Solomin, L, Cunningham, C. P., Pavlakis, G. N. und Felber, B. K. (1994) Elements distinct from human immunodeficiency virus type 1 splice sites are responsible for the Rev dependence of env mRNA, J. Virol. 68, 2986-2993

O'Reilly, M. M., McNally, M. T. und Beemon, K. L. (1995) Two strong 5' splice sites and competing, suboptimal 3' splice sites involved in alternative splicing of human immunodeficiency virus type 1 RNA, Virology 213, 373-385

Olsen, H. S., Cochrane, A. W. und Rosen, C. (1992) Interaction of cellular factors with intragenic cis-acting repressive sequences within the HIV genome, Virology 191, 709-715

Ono, A. und Freed, E. O. (2004) Cell-type-dependent targeting of human immunodeficiency virus type 1 assembly to the plasma membrane and the multivesicular body, J. Virol. 78, 1552-1563

Pollard, V. W. und Malim, M. H. (1998) The HIV-1 Rev protein [In Process Citation], Annu. Rev. Microbiol. 52:491-532, 491-532

Powell, D. M., Amaral, M. C., Wu, J. Y., Maniatis, T. und Greene, W. C. (1997) HIV Rev-dependent binding of SF2/ASF to the Rev response element: possible role in Rev-mediated inhibition of HIV RNA splicing, Proc. Natl. Acad. Sci. USA 94, 973-978

Ragheb, J. A., Couture, L., Mullen, C., Ridgway, A. und Morgan, R. A. (1999) Inhibition of human immunodeficiency virus type 1 by Tat/Rev-regulated expression of cytosine deaminase, interferon alpha2, or diphtheria toxin compared with inhibition by transdominant Rev, Hum. Gene Ther. 10, 103-112

Ratner, L., Fisher, A., Jagodzinski, L. L., Mitsuya, H., Liou, R. S., Gallo, R. C. und Wong Staal, F. (1987) Complete nucleotide sequences of functional clones of the AIDS virus, AIDS Res. Hum. Retroviruses 3, 57-69

Rosen, C. A., Terwilliger, E., Dayton, A., Sodroski, J. G. und Haseltine, W. A. (1988) Intragenic cis-acting art gene-responsive sequences of the human immunodeficiency virus, Proc. Natl. Acad. Sci. USA 85, 2071-2075

Schneider, R., Campbell, M., Nasioulas, G., Felber, B. K. und Pavlakis, G. N. (1997) Inactivation of the human immunodeficiency virus type 1 inhibitory elements allows Rev-independent expression of Gag and Gag/protease and particle formation, J. Virol: 71, 4892-4903

Schwartz, S., Campbell, M., Nasioulas, G., Harrison. J., Felber, B. K. und Pavlakis, G. N. (1992a) Mutational inactivation of an inhibitory sequence in human immunodeficiency virus type 1 results in Rev-independent gag expression, .J. Virol. 66, 7176-7182

Schwartz, S., Felber, B. K. und Pavlakis, G. N. (1992b) Distinct RNA sequences in the gag region of human immunodeficiency virus type 1 decrease RNA stability and inhibit expression in the absence of Rev protein, J. Virol. 66, 150-159

Smythe, J. A., Sun, D., Thomson, M., Markham, P. D., Reitz, M. S., Jr., Gallo, R. C. und Lisziewicz, J. (1994) A Rev-inducible mutant gag gene stably transferred into T lymphocytes: an approach to gene therapy against human immunodeficiency virus type 1 infection, Proc. Natl. Acad. Sci. USA 91, 3657-3661

Trono, D., Feinberg, M. B. und Baltimore, D. (1989) HIV-1 Gag mutants can dominantly interfere with the replication of the wild-type virus, Cell 59, 113-120 von Poblotzki, A., Wagner, R., Niedrig, M., Wanner, G., Wolf, H. und Modrow, S. (1993) Identification of a region in the Pr55gag-polyprotein essential for HIV-1 particle formation, Virology 193, 981-985

Wagner, R., Graf, M., Bieler, K., Wolf, H., Grunwald, T., Foley, P. und Uberla, K. (2000) Rev-independent expression of synthetic gag-pol genes of human immunodeficiency virus type 1 and simian immunodeficiency virus: implications for the safety of lentiviral vectors [In Process Citation], Hum Gene Ther 11, 2403-2413

Wilk, T., Gross, I., Gowen, B. E., Rutten, T., de Haas, F., Welker, R., Krausslich, H. G., Boulanger, P. und Fuller, S. D. (2001) Organization of immature human immunodeficiency virus type 1, J. Virol. 75, 759-771

Wolf, H., Modrow, S., Soutschek, E., Motz, M., Grunow, R. und Döbl, H. (1990) Production, mapping and biological characterisation of monoclonal antibodies to the core protein (p24) of the human immunodeficiency virus type 1., AIFO 1, 24-29

Zolotukhin, S., Potter, M., Hauswirth, W. W., Guy, J. und Muzyczka, N. (1996) A "humanized" green fluorescent protein cDNA adapted for high-level expression in mammalian cells, J. Virol. 70, 4646-4654

The invention claimed is:

1. An expression vector comprising:

(a) a target nucleic acid molecule comprising the nucleotide sequence of SEQ ID NO: 1, 16 or 18 that codes for a Trans-Dominant Negative (TDN) lentivirus protein; and (b) a promoter sequence inducible by a lentivirus Tat protein wherein the promoter sequence is in operative linkage with the target nucleic acid molecule, wherein the codon usage of the nucleic acid molecule according to (a) is matched to that of a mammal such that the TDN lentivirus protein is expressed at an early phase of HIV infection before expression of HIV structural proteins.

2. The expression vector of claim 1, wherein the promoter sequence is a lentiviral LTR sequence or a functional partial sequence thereof.

3. A cell transformed or transfected with the expression vector of claim 1.

4. A medicament comprising the expression vector of claim 1 and a pharmaceutically acceptable carrier.

5. A medicament comprising the cell of claim 3 and a pharmaceutically acceptable carrier.

* * * * *

SEQUENCE LISTING

```
<160> NUMBER OF SEQ ID NOS: 19

<210> SEQ ID NO 1
<211> LENGTH: 1143
<212> TYPE: DNA
<213> ORGANISM: Artificial sequence
<220> FEATURE:
<221> NAME/KEY: CDS
<222> LOCATION: (16)..(1125)
<223> OTHER INFORMATION: Nucleic acid molecule which encodes completely
      synthetic amino acid sequence of TDsyngag

<400> SEQUENCE: 1

gaattcgccg ccagc atg ggc gcc agg gcc agc gtg ctg agc ggc ggc gag      51
                 Met Gly Ala Arg Ala Ser Val Leu Ser Gly Gly Glu
                 1               5                   10

ctg gac agg tgg gag aag atc agg ctg agg ccc ggc ggc aag aag aag       99
Leu Asp Arg Trp Glu Lys Ile Arg Leu Arg Pro Gly Gly Lys Lys Lys
        15                  20                  25

tat aag ctg aag cac atc gtg tgg gcc agc agg gag ctg gag agg ttc      147
Tyr Lys Leu Lys His Ile Val Trp Ala Ser Arg Glu Leu Glu Arg Phe
    30                  35                  40

gcc gtg aac ccc ggc ctg ctg gag acc agc gag ggc tgc agg cag atc      195
Ala Val Asn Pro Gly Leu Leu Glu Thr Ser Glu Gly Cys Arg Gln Ile
45                  50                  55                  60

ctg ggc cag ctg cag ccc agc ctg cag acc ggc agc gag gag ctg agg      243
Leu Gly Gln Leu Gln Pro Ser Leu Gln Thr Gly Ser Glu Glu Leu Arg
                65                  70                  75

agc ctg tac aac acc gtg gcc acc ctg tac tgc gtg cac cag agg atc      291
Ser Leu Tyr Asn Thr Val Ala Thr Leu Tyr Cys Val His Gln Arg Ile
            80                  85                  90

gag atc aag gac acc aag gag gcc ctg ttc agc ccc gag gtg atc ccc      339
Glu Ile Lys Asp Thr Lys Glu Ala Leu Phe Ser Pro Glu Val Ile Pro
        95                  100                 105

atg ttc agc gcc ctg agc gag gga gcc acc ccc cag gac ctg aac acc      387
Met Phe Ser Ala Leu Ser Glu Gly Ala Thr Pro Gln Asp Leu Asn Thr
```

-continued

```
    110                 115                 120

atg ctg aac acc gtg ggc ggc cac cag gcc gcc atg cag atg ctg aag      435
Met Leu Asn Thr Val Gly Gly His Gln Ala Ala Met Gln Met Leu Lys
125                 130                 135                 140

gag acc atc aac gag gag gcc gcc gag tgg gac agg gtg cac ccc gtg      483
Glu Thr Ile Asn Glu Glu Ala Ala Glu Trp Asp Arg Val His Pro Val
                145                 150                 155

cac gcc ggc ccc atc gcc ccc ggc cag atg agg gag ccc cgc ggc agc      531
His Ala Gly Pro Ile Ala Pro Gly Gln Met Arg Glu Pro Arg Gly Ser
            160                 165                 170

gac atc gcc ggc acc acc agc acc ctg cag gag cag atc ggc tgg atg      579
Asp Ile Ala Gly Thr Thr Ser Thr Leu Gln Glu Gln Ile Gly Trp Met
        175                 180                 185

acc aac aac ccc ccc atc ccc gtg ggc gaa atc tac aag agg tgg atc      627
Thr Asn Asn Pro Pro Ile Pro Val Gly Glu Ile Tyr Lys Arg Trp Ile
    190                 195                 200

atc ctg ggc ctg aac aag atc gtg agg atg tac agc ccc acc agc atc      675
Ile Leu Gly Leu Asn Lys Ile Val Arg Met Tyr Ser Pro Thr Ser Ile
205                 210                 215                 220

ctg gat atc agg cag ggc ccc aaa gag ccc ttc agg gac tac gtg gac      723
Leu Asp Ile Arg Gln Gly Pro Lys Glu Pro Phe Arg Asp Tyr Val Asp
                225                 230                 235

agg ttc tac aag acc ctg cgc gcc gag cag gcc agc cag gag gtg aag      771
Arg Phe Tyr Lys Thr Leu Arg Ala Glu Gln Ala Ser Gln Glu Val Lys
            240                 245                 250

aac tgg atg acc gag acc ctg ctg gtg cag aac gcc aac ccc gac tgc      819
Asn Trp Met Thr Glu Thr Leu Leu Val Gln Asn Ala Asn Pro Asp Cys
        255                 260                 265

aag acc atc ctg aag gcc ctg gga ccc gcc gcc acc ctg gag gag atg      867
Lys Thr Ile Leu Lys Ala Leu Gly Pro Ala Ala Thr Leu Glu Glu Met
    270                 275                 280

atg acc gcc tgc cag ggc gtg ggc ggc ccc ggc cac aag gcc agg gtg      915
Met Thr Ala Cys Gln Gly Val Gly Gly Pro Gly His Lys Ala Arg Val
285                 290                 295                 300

ctg gcc gag gcc atg agc cag gtg acc aac acc gcc acc atc atg atg      963
Leu Ala Glu Ala Met Ser Gln Val Thr Asn Thr Ala Thr Ile Met Met
                305                 310                 315

cag agg ggc aac ttc agg aac cag agg aag atg gtg aag tgc ttc aac     1011
Gln Arg Gly Asn Phe Arg Asn Gln Arg Lys Met Val Lys Cys Phe Asn
            320                 325                 330

tgc ggc aag gag ggc cac acc gcc agg aac tgc cgc gcc ccc agg aag     1059
Cys Gly Lys Glu Gly His Thr Ala Arg Asn Cys Arg Ala Pro Arg Lys
        335                 340                 345

aag ggc tgc tgg aag tgc ggc aag gag ggc cac cag atg aag gac tgc     1107
Lys Gly Cys Trp Lys Cys Gly Lys Glu Gly His Gln Met Lys Asp Cys
    350                 355                 360

acc gag agg cag gcc aac taatagtccg gactcgag                         1143
Thr Glu Arg Gln Ala Asn
365                 370


<210> SEQ ID NO 2
<211> LENGTH: 370
<212> TYPE: PRT
<213> ORGANISM: Artificial sequence
<220> FEATURE:
<223> OTHER INFORMATION: Completely synthetic protein

<400> SEQUENCE: 2

Met Gly Ala Arg Ala Ser Val Leu Ser Gly Gly Glu Leu Asp Arg Trp
  1               5                  10                  15

Glu Lys Ile Arg Leu Arg Pro Gly Gly Lys Lys Lys Tyr Lys Leu Lys
```

```
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
 65                 70                  75                  80

Thr Val Ala Thr Leu Tyr Cys Val His Gln Arg Ile Glu Ile Lys Asp
                85                  90                  95

Thr Lys Glu Ala Leu Phe Ser Pro Glu Val Ile Pro Met Phe Ser Ala
            100                 105                 110

Leu Ser Glu Gly Ala Thr Pro Gln Asp Leu Asn Thr Met Leu Asn Thr
        115                 120                 125

Val Gly Gly His Gln Ala Ala Met Gln Met Leu Lys Glu Thr Ile Asn
    130                 135                 140

Glu Glu Ala Ala Glu Trp Asp Arg Val His Pro Val His Ala Gly Pro
145                 150                 155                 160

Ile Ala Pro Gly Gln Met Arg Glu Pro Arg Gly Ser Asp Ile Ala Gly
                165                 170                 175

Thr Thr Ser Thr Leu Gln Glu Gln Ile Gly Trp Met Thr Asn Asn Pro
            180                 185                 190

Pro Ile Pro Val Gly Glu Ile Tyr Lys Arg Trp Ile Ile Leu Gly Leu
        195                 200                 205

Asn Lys Ile Val Arg Met Tyr Ser Pro Thr Ser Ile Leu Asp Ile Arg
    210                 215                 220

Gln Gly Pro Lys Glu Pro Phe Arg Asp Tyr Val Asp Arg Phe Tyr Lys
225                 230                 235                 240

Thr Leu Arg Ala Glu Gln Ala Ser Gln Glu Val Lys Asn Trp Met Thr
                245                 250                 255

Glu Thr Leu Leu Val Gln Asn Ala Asn Pro Asp Cys Lys Thr Ile Leu
            260                 265                 270

Lys Ala Leu Gly Pro Ala Ala Thr Leu Glu Glu Met Met Thr Ala Cys
        275                 280                 285

Gln Gly Val Gly Gly Pro Gly His Lys Ala Arg Val Leu Ala Glu Ala
    290                 295                 300

Met Ser Gln Val Thr Asn Thr Ala Thr Ile Met Met Gln Arg Gly Asn
305                 310                 315                 320

Phe Arg Asn Gln Arg Lys Met Val Lys Cys Phe Asn Cys Gly Lys Glu
                325                 330                 335

Gly His Thr Ala Arg Asn Cys Arg Ala Pro Arg Lys Lys Gly Cys Trp
            340                 345                 350

Lys Cys Gly Lys Glu Gly His Gln Met Lys Asp Cys Thr Glu Arg Gln
        355                 360                 365

Ala Asn
    370
```

```
<210> SEQ ID NO 3
<211> LENGTH: 1113
<212> TYPE: DNA
<213> ORGANISM: Artificial sequence
<220> FEATURE:
<223> OTHER INFORMATION: Nucleotide molecule which encodes a
      completely synthetic protein
<221> NAME/KEY: CDS
<222> LOCATION: (1)..(1113)

<400> SEQUENCE: 3
```

-continued

```
atg ggt gcg aga gcg tca gta tta agc ggg gga gaa tta gat cga tgg        48
Met Gly Ala Arg Ala Ser Val Leu Ser Gly Gly Glu Leu Asp Arg Trp
  1               5                  10                  15

gaa aaa att cgg tta agg cca ggg gga aag aaa aaa tat aaa tta aaa        96
Glu Lys Ile Arg Leu Arg Pro Gly Gly Lys Lys Lys Tyr Lys Leu Lys
             20                  25                  30

cat ata gta tgg gca agc agg gag cta gaa cga ttc gca gtt aat cct       144
His Ile Val Trp Ala Ser Arg Glu Leu Glu Arg Phe Ala Val Asn Pro
         35                  40                  45

ggc ctg tta gaa aca tca gaa ggc tgt aga caa ata ctg gga cag cta       192
Gly Leu Leu Glu Thr Ser Glu Gly Cys Arg Gln Ile Leu Gly Gln Leu
     50                  55                  60

caa cca tcc ctt cag aca gga tca gaa gaa ctt aga tca tta tat aat       240
Gln Pro Ser Leu Gln Thr Gly Ser Glu Glu Leu Arg Ser Leu Tyr Asn
 65                  70                  75                  80

aca gta gca acc ctc tat tgt gtg cat caa agg ata gag ata aaa gac       288
Thr Val Ala Thr Leu Tyr Cys Val His Gln Arg Ile Glu Ile Lys Asp
                 85                  90                  95

acc aag gaa gct tta ttc agc cca gaa gta ata ccc atg ttt tca gca       336
Thr Lys Glu Ala Leu Phe Ser Pro Glu Val Ile Pro Met Phe Ser Ala
            100                 105                 110

tta tca gaa gga gcc acc cca caa gat tta aac acc atg cta aac aca       384
Leu Ser Glu Gly Ala Thr Pro Gln Asp Leu Asn Thr Met Leu Asn Thr
        115                 120                 125

gtg ggg gga cat caa gca gcc atg caa atg tta aaa gag acc atc aat       432
Val Gly Gly His Gln Ala Ala Met Gln Met Leu Lys Glu Thr Ile Asn
    130                 135                 140

gag gaa gct gca gaa tgg gat aga gta cat cca gtg cat gca ggg cct       480
Glu Glu Ala Ala Glu Trp Asp Arg Val His Pro Val His Ala Gly Pro
145                 150                 155                 160

att gca cca ggc cag atg aga gaa cca agg gga agt gac ata gca gga       528
Ile Ala Pro Gly Gln Met Arg Glu Pro Arg Gly Ser Asp Ile Ala Gly
                165                 170                 175

act act agt acc ctt cag gaa caa ata gga tgg atg aca aat aat cca       576
Thr Thr Ser Thr Leu Gln Glu Gln Ile Gly Trp Met Thr Asn Asn Pro
            180                 185                 190

cct atc cca gta gga gaa att tat aaa aga tgg ata atc ctg gga tta       624
Pro Ile Pro Val Gly Glu Ile Tyr Lys Arg Trp Ile Ile Leu Gly Leu
        195                 200                 205

aat aaa ata gta aga atg tat agc cct acc agc att ctg gac ata aga       672
Asn Lys Ile Val Arg Met Tyr Ser Pro Thr Ser Ile Leu Asp Ile Arg
    210                 215                 220

caa gga cca aaa gaa cct ttt aga gac tat gta gac cgg ttc tat aaa       720
Gln Gly Pro Lys Glu Pro Phe Arg Asp Tyr Val Asp Arg Phe Tyr Lys
225                 230                 235                 240

act cta aga gcc gag caa gct tca cag gag gta aaa aat tgg atg aca       768
Thr Leu Arg Ala Glu Gln Ala Ser Gln Glu Val Lys Asn Trp Met Thr
                245                 250                 255

gaa acc ttg ttg gtc caa aat gcg aac cca gat tgt aag act att tta       816
Glu Thr Leu Leu Val Gln Asn Ala Asn Pro Asp Cys Lys Thr Ile Leu
            260                 265                 270

aaa gca ttg gga cca gcg gct aca cta gaa gaa atg atg aca gca tgt       864
Lys Ala Leu Gly Pro Ala Ala Thr Leu Glu Glu Met Met Thr Ala Cys
        275                 280                 285

cag gga gta gga gga ccc ggc cat aag gca aga gtt ttg gct gaa gca       912
Gln Gly Val Gly Gly Pro Gly His Lys Ala Arg Val Leu Ala Glu Ala
    290                 295                 300

atg agc caa gta aca aat aca gct acc ata atg atg cag aga ggc aat       960
Met Ser Gln Val Thr Asn Thr Ala Thr Ile Met Met Gln Arg Gly Asn
305                 310                 315                 320
```

```
ttt agg aac caa aga aag atg gtt aag tgt ttc aat tgt ggc aaa gaa      1008
Phe Arg Asn Gln Arg Lys Met Val Lys Cys Phe Asn Cys Gly Lys Glu
                325                 330                 335

ggg cac aca gcc aga aat tgc agg gcc cct agg aaa aag ggc tgt tgg      1056
Gly His Thr Ala Arg Asn Cys Arg Ala Pro Arg Lys Lys Gly Cys Trp
            340                 345                 350

aaa tgt gga aag gaa gga cac caa atg aaa gat tgt act gag aga cag      1104
Lys Cys Gly Lys Glu Gly His Gln Met Lys Asp Cys Thr Glu Arg Gln
        355                 360                 365

gct aat taa                                                          1113
Ala Asn
    370


<210> SEQ ID NO 4
<211> LENGTH: 370
<212> TYPE: PRT
<213> ORGANISM: Artificial sequence
<220> FEATURE:
<223> OTHER INFORMATION: Completely synthetic sequence

<400> SEQUENCE: 4

Met Gly Ala Arg Ala Ser Val Leu Ser Gly Gly Glu Leu Asp Arg Trp
  1               5                  10                  15

Glu Lys Ile Arg Leu Arg Pro Gly Gly Lys Lys Lys Tyr Lys Leu Lys
             20                  25                  30

His Ile Val Trp Ala Ser Arg Glu Leu Glu Arg Phe Ala Val Asn Pro
         35                  40                  45

Gly Leu Leu Glu Thr Ser Glu Gly Cys Arg Gln Ile Leu Gly Gln Leu
     50                  55                  60

Gln Pro Ser Leu Gln Thr Gly Ser Glu Glu Leu Arg Ser Leu Tyr Asn
 65                  70                  75                  80

Thr Val Ala Thr Leu Tyr Cys Val His Gln Arg Ile Glu Ile Lys Asp
                 85                  90                  95

Thr Lys Glu Ala Leu Phe Ser Pro Glu Val Ile Pro Met Phe Ser Ala
            100                 105                 110

Leu Ser Glu Gly Ala Thr Pro Gln Asp Leu Asn Thr Met Leu Asn Thr
        115                 120                 125

Val Gly Gly His Gln Ala Ala Met Gln Met Leu Lys Glu Thr Ile Asn
    130                 135                 140

Glu Glu Ala Ala Glu Trp Asp Arg Val His Pro Val His Ala Gly Pro
145                 150                 155                 160

Ile Ala Pro Gly Gln Met Arg Glu Pro Arg Gly Ser Asp Ile Ala Gly
                165                 170                 175

Thr Thr Ser Thr Leu Gln Glu Gln Ile Gly Trp Met Thr Asn Asn Pro
            180                 185                 190

Pro Ile Pro Val Gly Glu Ile Tyr Lys Arg Trp Ile Ile Leu Gly Leu
        195                 200                 205

Asn Lys Ile Val Arg Met Tyr Ser Pro Thr Ser Ile Leu Asp Ile Arg
    210                 215                 220

Gln Gly Pro Lys Glu Pro Phe Arg Asp Tyr Val Asp Arg Phe Tyr Lys
225                 230                 235                 240

Thr Leu Arg Ala Glu Gln Ala Ser Gln Glu Val Lys Asn Trp Met Thr
                245                 250                 255

Glu Thr Leu Leu Val Gln Asn Ala Asn Pro Asp Cys Lys Thr Ile Leu
            260                 265                 270

Lys Ala Leu Gly Pro Ala Ala Thr Leu Glu Glu Met Met Thr Ala Cys
        275                 280                 285
```

```
Gln Gly Val Gly Gly Pro Gly His Lys Ala Arg Val Leu Ala Glu Ala
    290                 295                 300

Met Ser Gln Val Thr Asn Thr Ala Thr Ile Met Met Gln Arg Gly Asn
305                 310                 315                 320

Phe Arg Asn Gln Arg Lys Met Val Lys Cys Phe Asn Cys Gly Lys Glu
                325                 330                 335

Gly His Thr Ala Arg Asn Cys Arg Ala Pro Arg Lys Lys Gly Cys Trp
            340                 345                 350

Lys Cys Gly Lys Glu Gly His Gln Met Lys Asp Cys Thr Glu Arg Gln
        355                 360                 365

Ala Asn
    370


<210> SEQ ID NO 5
<211> LENGTH: 18
<212> TYPE: DNA
<213> ORGANISM: Artificial sequence
<220> FEATURE:
<223> OTHER INFORMATION: Description of the artificial sequence: primer
      5'-3
<220> FEATURE:
<223> OTHER INFORMATION: DEL1

<400> SEQUENCE: 5

taaagcttcc ttggtgtc                                                    18


<210> SEQ ID NO 6
<211> LENGTH: 20
<212> TYPE: DNA
<213> ORGANISM: Artificial sequence
<220> FEATURE:
<223> OTHER INFORMATION: Description of the artificial sequence: primer
      5'-3
<220> FEATURE:
<223> OTHER INFORMATION: Del2

<400> SEQUENCE: 6

ttcagcccag aagtaatacc                                                  20


<210> SEQ ID NO 7
<211> LENGTH: 27
<212> TYPE: DNA
<213> ORGANISM: Artificial sequence
<220> FEATURE:
<223> OTHER INFORMATION: Description of the artificial sequence: primer
      5'-3
<220> FEATURE:
<223> OTHER INFORMATION: Del3

<400> SEQUENCE: 7

tacaagaccc tgcgcgccga gcaggcc                                          27


<210> SEQ ID NO 8
<211> LENGTH: 27
<212> TYPE: DNA
<213> ORGANISM: Artificial sequence
<220> FEATURE:
<223> OTHER INFORMATION: Description of the artificial sequence: primer
      5'-3
<220> FEATURE:
<223> OTHER INFORMATION: Del4

<400> SEQUENCE: 8

ctccctcatc tggccggggg cgatggg                                          27
```

-continued

<210> SEQ ID NO 9
<211> LENGTH: 27
<212> TYPE: DNA
<213> ORGANISM: Artificial sequence
<220> FEATURE:
<223> OTHER INFORMATION: Description of the artificial sequence: primer 5'-3
<220> FEATURE:
<223> OTHER INFORMATION: Del5

<400> SEQUENCE: 9
ttctctcatc tggcctggtg caatagg 27

<210> SEQ ID NO 10
<211> LENGTH: 27
<212> TYPE: DNA
<213> ORGANISM: Artificial sequence
<220> FEATURE:
<223> OTHER INFORMATION: Description of the artificial sequence: primer 5'-3
<220> FEATURE:
<223> OTHER INFORMATION: Del6

<400> SEQUENCE: 10
tataaaactc taagagccga gcaagct 27

<210> SEQ ID NO 11
<211> LENGTH: 44
<212> TYPE: DNA
<213> ORGANISM: Artificial sequence
<220> FEATURE:
<223> OTHER INFORMATION: Description of the artificial sequence: primer 5'-3
<220> FEATURE:
<223> OTHER INFORMATION: Gag-stop1

<400> SEQUENCE: 11
ggaaggccag atcttccctc attaattagc ctgtctctca gtac 44

<210> SEQ ID NO 12
<211> LENGTH: 44
<212> TYPE: DNA
<213> ORGANISM: Artificial sequence
<220> FEATURE:
<223> OTHER INFORMATION: Description of the artificial sequence: primer 5'-3
<220> FEATURE:
<223> OTHER INFORMATION: Gag-stop2

<400> SEQUENCE: 12
gtactgagag acaggctaat taatgaggga agatctggcc ttcc 44

<210> SEQ ID NO 13
<211> LENGTH: 35
<212> TYPE: DNA
<213> ORGANISM: Artificial sequence
<220> FEATURE:
<223> OTHER INFORMATION: Description of the artificial sequence: primer 5'-3
<220> FEATURE:
<223> OTHER INFORMATION: ltr1

<400> SEQUENCE: 13
attgtcgaca cgcgttggaa gggctaattc actcc 35

<210> SEQ ID NO 14
<211> LENGTH: 27
<212> TYPE: DNA
<213> ORGANISM: Artificial sequence
<220> FEATURE:

```
<223> OTHER INFORMATION: Description of the artificial sequence: primer
      5'-3
<220> FEATURE:
<223> OTHER INFORMATION: ltr2

<400> SEQUENCE: 14

attgaattcc tctctccttc tagcctc                                          27


<210> SEQ ID NO 15
<211> LENGTH: 18
<212> TYPE: DNA
<213> ORGANISM: Artificial sequence
<220> FEATURE:
<223> OTHER INFORMATION: Description of the artificial sequence: primer
      5'-3
<220> FEATURE:
<223> OTHER INFORMATION: ltr3

<400> SEQUENCE: 15

gcttgcccat actatatg                                                    18


<210> SEQ ID NO 16
<211> LENGTH: 900
<212> TYPE: DNA
<213> ORGANISM: Artificial sequence
<220> FEATURE:
<223> OTHER INFORMATION: Description of the artificial sequence:
      completely synthetic gene
<220> FEATURE:
<221> NAME/KEY: CDS
<222> LOCATION: (1)..(900)
<220> FEATURE:
<223> OTHER INFORMATION: Completely artificial sequence

<400> SEQUENCE: 16

atg ggc gcc agg gcc agc gtg ctg agc ggc ggc gag ctg gac agg tgg        48
Met Gly Ala Arg Ala Ser Val Leu Ser Gly Gly Glu Leu Asp Arg Trp
  1               5                  10                  15

gag aag atc agg ctg agg ccc ggc ggc aag aag aag tat aag ctg aag        96
Glu Lys Ile Arg Leu Arg Pro Gly Gly Lys Lys Lys Tyr Lys Leu Lys
             20                  25                  30

cac atc gtg tgg gcc agc agg gag ctg gag agg ttc gcc gtg aac ccc       144
His Ile Val Trp Ala Ser Arg Glu Leu Glu Arg Phe Ala Val Asn Pro
         35                  40                  45

ggc ctg ctg gag acc agc gag ggc tgc agg cag atc ctg ggc cag ctg       192
Gly Leu Leu Glu Thr Ser Glu Gly Cys Arg Gln Ile Leu Gly Gln Leu
     50                  55                  60

cag ccc agc ctg cag acc ggc agc gag gag ctg agg agc ctg tac aac       240
Gln Pro Ser Leu Gln Thr Gly Ser Glu Glu Leu Arg Ser Leu Tyr Asn
 65                  70                  75                  80

acc gtg gcc acc ctg tac tgc gtg cac cag agg atc gag atc aag gac       288
Thr Val Ala Thr Leu Tyr Cys Val His Gln Arg Ile Glu Ile Lys Asp
                 85                  90                  95

acc aag gag gcc ctg ttc agc ccc gag gtg atc ccc atg ttc agc gcc       336
Thr Lys Glu Ala Leu Phe Ser Pro Glu Val Ile Pro Met Phe Ser Ala
            100                 105                 110

ctg agc gag gga gcc acc ccc cag gac ctg aac acc atg ctg aac acc       384
Leu Ser Glu Gly Ala Thr Pro Gln Asp Leu Asn Thr Met Leu Asn Thr
        115                 120                 125

gtg ggc ggc cac cag gcc gcc atg cag atg ctg aag gag acc atc aac       432
Val Gly Gly His Gln Ala Ala Met Gln Met Leu Lys Glu Thr Ile Asn
    130                 135                 140

gag gag gcc gcc gag tgg gac agg gtg cac ccc gtg cac gcc ggc ccc       480
Glu Glu Ala Ala Glu Trp Asp Arg Val His Pro Val His Ala Gly Pro
145                 150                 155                 160
```

-continued

```
atc gcc ccc ggc cag atg agg gag tac aag acc ctg cgc gcc gag cag      528
Ile Ala Pro Gly Gln Met Arg Glu Tyr Lys Thr Leu Arg Ala Glu Gln
                165                 170                 175

gcc agc cag gag gtg aag aac tgg atg acc gag acc ctg ctg gtg cag      576
Ala Ser Gln Glu Val Lys Asn Trp Met Thr Glu Thr Leu Leu Val Gln
            180                 185                 190

aac gcc aac ccc gac tgc aag acc atc ctg aag gcc ctg gga ccc gcc      624
Asn Ala Asn Pro Asp Cys Lys Thr Ile Leu Lys Ala Leu Gly Pro Ala
        195                 200                 205

gcc acc ctg gag gag atg atg acc gcc tgc cag ggc gtg ggc ggc ccc      672
Ala Thr Leu Glu Glu Met Met Thr Ala Cys Gln Gly Val Gly Gly Pro
    210                 215                 220

ggc cac aag gcc agg gtg ctg gcc gag gcc atg agc cag gtg acc aac      720
Gly His Lys Ala Arg Val Leu Ala Glu Ala Met Ser Gln Val Thr Asn
225                 230                 235                 240

acc gcc acc atc atg atg cag agg ggc aac ttc agg aac cag agg aag      768
Thr Ala Thr Ile Met Met Gln Arg Gly Asn Phe Arg Asn Gln Arg Lys
                245                 250                 255

atg gtg aag tgc ttc aac tgc ggc aag gag ggc cac acc gcc agg aac      816
Met Val Lys Cys Phe Asn Cys Gly Lys Glu Gly His Thr Ala Arg Asn
            260                 265                 270

tgc cgc gcc ccc agg aag aag ggc tgc tgg aag tgc ggc aag gag ggc      864
Cys Arg Ala Pro Arg Lys Lys Gly Cys Trp Lys Cys Gly Lys Glu Gly
        275                 280                 285

cac cag atg aag gac tgc acc gag agg cag gcc aac                      900
His Gln Met Lys Asp Cys Thr Glu Arg Gln Ala Asn
    290                 295                 300


<210> SEQ ID NO 17
<211> LENGTH: 300
<212> TYPE: PRT
<213> ORGANISM: Artificial sequence
<220> FEATURE:
<223> OTHER INFORMATION: Completely synthetic protein syquence TDsyngag
      delta 2

<400> SEQUENCE: 17

Met Gly Ala Arg Ala Ser Val Leu Ser Gly Gly Glu Leu Asp Arg Trp
  1               5                  10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
     50                  55                  60

Gln Pro Ser Leu Gln Thr Gly Ser Glu Glu Leu Arg Ser Leu Tyr Asn
 65                  70                  75                  80

Thr Val Ala Thr Leu Tyr Cys Val His Gln Arg Ile Glu Ile Lys Asp
                85                  90                  95

Thr Lys Glu Ala Leu Phe Ser Pro Glu Val Ile Pro Met Phe Ser Ala
            100                 105                 110

Leu Ser Glu Gly Ala Thr Pro Gln Asp Leu Asn Thr Met Leu Asn Thr
        115                 120                 125

Val Gly Gly His Gln Ala Ala Met Gln Met Leu Lys Glu Thr Ile Asn
    130                 135                 140

Glu Glu Ala Ala Glu Trp Asp Arg Val His Pro Val His Ala Gly Pro
145                 150                 155                 160

Ile Ala Pro Gly Gln Met Arg Glu Tyr Lys Thr Leu Arg Ala Glu Gln
                165                 170                 175
```

-continued

```
Ala Ser Gln Glu Val Lys Asn Trp Met Thr Glu Thr Leu Leu Val Gln
            180                 185                 190

Asn Ala Asn Pro Asp Cys Lys Thr Ile Leu Lys Ala Leu Gly Pro Ala
        195                 200                 205

Ala Thr Leu Glu Glu Met Met Thr Ala Cys Gln Gly Val Gly Gly Pro
    210                 215                 220

Gly His Lys Ala Arg Val Leu Ala Glu Ala Met Ser Gln Val Thr Asn
225                 230                 235                 240

Thr Ala Thr Ile Met Met Gln Arg Gly Asn Phe Arg Asn Gln Arg Lys
                245                 250                 255

Met Val Lys Cys Phe Asn Cys Gly Lys Glu Gly His Thr Ala Arg Asn
            260                 265                 270

Cys Arg Ala Pro Arg Lys Lys Gly Cys Trp Lys Cys Gly Lys Glu Gly
        275                 280                 285

His Gln Met Lys Asp Cys Thr Glu Arg Gln Ala Asn
    290                 295                 300


<210> SEQ ID NO 18
<211> LENGTH: 900
<212> TYPE: DNA
<213> ORGANISM: Artificial sequence
<220> FEATURE:
<223> OTHER INFORMATION: Description of the artificial sequence:
      completely synthetic gene
<220> FEATURE:
<221> NAME/KEY: CDS
<222> LOCATION: (1)..(900)
<220> FEATURE:
<223> OTHER INFORMATION: TDsyngag delta 2 delta p7

<400> SEQUENCE: 18

atg ggc gcc agg gcc agc gtg ctg agc ggc ggc gag ctg gac agg tgg       48
Met Gly Ala Arg Ala Ser Val Leu Ser Gly Gly Glu Leu Asp Arg Trp
  1               5                  10                  15

gag aag atc agg ctg agg ccc ggc ggc aag aag aag tat aag ctg aag       96
Glu Lys Ile Arg Leu Arg Pro Gly Gly Lys Lys Lys Tyr Lys Leu Lys
             20                  25                  30

cac atc gtg tgg gcc agc agg gag ctg gag agg ttc gcc gtg aac ccc      144
His Ile Val Trp Ala Ser Arg Glu Leu Glu Arg Phe Ala Val Asn Pro
         35                  40                  45

ggc ctg ctg gag acc agc gag ggc tgc agg cag atc ctg ggc cag ctg      192
Gly Leu Leu Glu Thr Ser Glu Gly Cys Arg Gln Ile Leu Gly Gln Leu
     50                  55                  60

cag ccc agc ctg cag acc ggc agc gag gag ctg agg agc ctg tac aac      240
Gln Pro Ser Leu Gln Thr Gly Ser Glu Glu Leu Arg Ser Leu Tyr Asn
 65                  70                  75                  80

acc gtg gcc acc ctg tac tgc gtg cac cag agg atc gag atc aag gac      288
Thr Val Ala Thr Leu Tyr Cys Val His Gln Arg Ile Glu Ile Lys Asp
                 85                  90                  95

acc aag gag gcc ctg ttc agc ccc gag gtg atc ccc atg ttc agc gcc      336
Thr Lys Glu Ala Leu Phe Ser Pro Glu Val Ile Pro Met Phe Ser Ala
            100                 105                 110

ctg agc gag gga gcc acc ccc cag gac ctg aac acc atg ctg aac acc      384
Leu Ser Glu Gly Ala Thr Pro Gln Asp Leu Asn Thr Met Leu Asn Thr
        115                 120                 125

gtg ggc ggc cac cag gcc gcc atg cag atg ctg aag gag acc atc aac      432
Val Gly Gly His Gln Ala Ala Met Gln Met Leu Lys Glu Thr Ile Asn
    130                 135                 140

gag gag gcc gcc gag tgg gac agg gtg cac ccc gtg cac gcc ggc ccc      480
Glu Glu Ala Ala Glu Trp Asp Arg Val His Pro Val His Ala Gly Pro
145                 150                 155                 160
```

```
atc gcc ccc ggc cag atg agg gag tac aag acc ctg cgc gcc gag cag       528
Ile Ala Pro Gly Gln Met Arg Glu Tyr Lys Thr Leu Arg Ala Glu Gln
                165                 170                 175

gcc agc cag gag gtg aag aac tgg atg acc gag acc ctg ctg gtg cag       576
Ala Ser Gln Glu Val Lys Asn Trp Met Thr Glu Thr Leu Leu Val Gln
            180                 185                 190

aac gcc aac ccc gac tgc aag acc atc ctg aag gcc ctg gga ccc gcc       624
Asn Ala Asn Pro Asp Cys Lys Thr Ile Leu Lys Ala Leu Gly Pro Ala
        195                 200                 205

gcc acc ctg gag gag atg atg acc gcc tgc cag ggc gtg ggc ggc ccc       672
Ala Thr Leu Glu Glu Met Met Thr Ala Cys Gln Gly Val Gly Gly Pro
    210                 215                 220

ggc cac aag gcc agg gtg ctg gcc gag gcc atg agc cag gtg acc aac       720
Gly His Lys Ala Arg Val Leu Ala Glu Ala Met Ser Gln Val Thr Asn
225                 230                 235                 240

acc gcc acc atc atg atg cag agg ggc aac ttc agg aac cag agg aag       768
Thr Ala Thr Ile Met Met Gln Arg Gly Asn Phe Arg Asn Gln Arg Lys
                245                 250                 255

atg gtg aag tgc ttc aac tgc ggc aag gag ggc cac acc gcc agg aac       816
Met Val Lys Cys Phe Asn Cys Gly Lys Glu Gly His Thr Ala Arg Asn
            260                 265                 270

tgc cgc gcc ccc agg aag aag ggc tgc tgg aag tgc ggc aag gag ggc       864
Cys Arg Ala Pro Arg Lys Lys Gly Cys Trp Lys Cys Gly Lys Glu Gly
        275                 280                 285

cac cag atg aag gac tgc acc gag agg cag gcc aac                       900
His Gln Met Lys Asp Cys Thr Glu Arg Gln Ala Asn
    290                 295                 300
```

<210> SEQ ID NO 19
<211> LENGTH: 300
<212> TYPE: PRT
<213> ORGANISM: Artificial sequence
<220> FEATURE:
<223> OTHER INFORMATION: TDsyngag delta 2 delta p7

<400> SEQUENCE: 19

```
Met Gly Ala Arg Ala Ser Val Leu Ser Gly Gly Glu Leu Asp Arg Trp
  1               5                  10                  15

Glu Lys Ile Arg Leu Arg Pro Gly Gly Lys Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
     50                  55                  60

Gln Pro Ser Leu Gln Thr Gly Ser Glu Glu Leu Arg Ser Leu Tyr Asn
 65                  70                  75                  80

Thr Val Ala Thr Leu Tyr Cys Val His Gln Arg Ile Glu Ile Lys Asp
                85                  90                  95

Thr Lys Glu Ala Leu Phe Ser Pro Glu Val Ile Pro Met Phe Ser Ala
            100                 105                 110

Leu Ser Glu Gly Ala Thr Pro Gln Asp Leu Asn Thr Met Leu Asn Thr
        115                 120                 125

Val Gly Gly His Gln Ala Ala Met Gln Met Leu Lys Glu Thr Ile Asn
    130                 135                 140

Glu Glu Ala Ala Glu Trp Asp Arg Val His Pro Val His Ala Gly Pro
145                 150                 155                 160

Ile Ala Pro Gly Gln Met Arg Glu Tyr Lys Thr Leu Arg Ala Glu Gln
                165                 170                 175

Ala Ser Gln Glu Val Lys Asn Trp Met Thr Glu Thr Leu Leu Val Gln
```

-continued

```
            180                 185                 190

Asn Ala Asn Pro Asp Cys Lys Thr Ile Leu Lys Ala Leu Gly Pro Ala
        195                 200                 205

Ala Thr Leu Glu Glu Met Met Thr Ala Cys Gln Gly Val Gly Gly Pro
    210                 215                 220

Gly His Lys Ala Arg Val Leu Ala Glu Ala Met Ser Gln Val Thr Asn
225                 230                 235                 240

Thr Ala Thr Ile Met Met Gln Arg Gly Asn Phe Arg Asn Gln Arg Lys
                245                 250                 255

Met Val Lys Cys Phe Asn Cys Gly Lys Glu Gly His Thr Ala Arg Asn
            260                 265                 270

Cys Arg Ala Pro Arg Lys Lys Gly Cys Trp Lys Cys Gly Lys Glu Gly
        275                 280                 285

His Gln Met Lys Asp Cys Thr Glu Arg Gln Ala Asn
    290                 295                 300
```